US009757394B2

(12) United States Patent
Pipho et al.

(10) Patent No.: US 9,757,394 B2
(45) Date of Patent: Sep. 12, 2017

(54) SPIRONOLACTONE AQUEOUS FORMULATIONS

(71) Applicant: CMP DEVELOPMENT LLC, Farmville, NC (US)

(72) Inventors: Anthony Pipho, Winterville, NC (US); Michael Paul DeHart, Winterville, NC (US)

(73) Assignee: CMP DEVELOPMENT LLC, Farmville, NC (US)

( * ) Notice: Subject to any disclaimer, the term of this patent is extended or adjusted under 35 U.S.C. 154(b) by 0 days.

(21) Appl. No.: 15/337,559

(22) Filed: Oct. 28, 2016

(65) Prior Publication Data

US 2017/0119796 A1   May 4, 2017

Related U.S. Application Data

(60) Provisional application No. 62/495,583, filed on Oct. 30, 2015.

(51) Int. Cl.
| | |
|---|---|
| *A61K 31/585* | (2006.01) |
| *A61K 47/02* | (2006.01) |
| *A61K 47/10* | (2017.01) |
| *A61K 47/12* | (2006.01) |
| *A61K 47/24* | (2006.01) |
| *A61K 47/34* | (2017.01) |
| *A61K 47/36* | (2006.01) |
| *A61K 9/10* | (2006.01) |
| *A61K 9/107* | (2006.01) |
| *A61K 9/00* | (2006.01) |

(52) U.S. Cl.
CPC .......... *A61K 31/585* (2013.01); *A61K 9/0095* (2013.01); *A61K 9/107* (2013.01); *A61K 47/02* (2013.01); *A61K 47/10* (2013.01); *A61K 47/12* (2013.01); *A61K 47/24* (2013.01); *A61K 47/34* (2013.01); *A61K 47/36* (2013.01); *A61K 9/10* (2013.01)

(58) Field of Classification Search
CPC ...... A61K 31/585; A61K 47/02; A61K 47/10; A61K 47/12; A61K 47/24; A61K 47/34; A61K 47/36; A61K 9/0095; A61K 9/10; A61K 9/107
See application file for complete search history.

(56) References Cited

U.S. PATENT DOCUMENTS

| | | | |
|---|---|---|---|
| 4,837,211 A | 6/1989 | Olsen | |
| 7,300,670 B2 | 11/2007 | Venus | |
| 2003/0021841 A1 | 1/2003 | Matharu et al. | |
| 2006/0067892 A1 | 3/2006 | Vergnault | |
| 2006/0165614 A1* | 7/2006 | Nelson | A61K 9/5068 424/50 |
| 2006/0165807 A1* | 7/2006 | Castan | A61K 9/5015 424/490 |
| 2008/0069779 A1* | 3/2008 | Tamarkin | A61K 8/046 424/45 |
| 2008/0069886 A1 | 3/2008 | Vergnault | |
| 2011/0117205 A1 | 5/2011 | Castan et al. | |
| 2013/0039871 A1 | 2/2013 | Murata et al. | |

FOREIGN PATENT DOCUMENTS

WO     2007086078 A2    8/2007

OTHER PUBLICATIONS

Salgado et al. "Stability of spironolactone in an extemporaneously prepared aqueous suspension: the importance of microbiological quality of compounded paediatric formulations" The European Journal of Hospital Pharmacy Science, 2005, vol. 11, issue 3, pp. 68-73.*
Steele et al. "Understanding the World of Viscosity: A Tutorial on Rheology" ASHA Convention Presentation Slides, 2008, Chicago, IL, pp. 1-34.*
M. L. Buck, The Annals of Pharmacotherapy (2005) 39(5): 823-828.
Gupta et al., American Journal of Hospital Pharmacy (1978) 35(11): 1382-1385.
Mathur et al., American Journal of Hospital Pharmacy (1989) 46(10): 2040-2042.
Pramar et al., Journal of Clinical Pharmacy and Therapeutics (1992) 17(4): 245-248.
Nahata et al., The Annals of Pharmacotherapy (1993) 27(10): 1198-1199.
Allen et al., American Journal of Health-System Pharmacy (1996) 53(19): 2304-2309.
Basusarkar et al. International Journal of Pharmaceutical Review and Research (2013) 23(1): 67-70.
Kaukonen et al., Journal of Pharmacy and Pharmacology (1998) 50(6): 611-619.
Flynn, Buffers—pH Control within Pharmaceutical Systems, J. Parenteral Drug Assoc. (1980) 34(2): 139-162.
Xu et al., Arzneimittel Forschung (2008) 58(3): 117-121.
Pramar et al., Drug Development and Industrial Pharmacy (1991) 17(5): 747-761.
Pramar et al., J. Pharm. Sci. (1991) 80(6): 551-553.
USPA905, Uniformity of Dosage Units, Feb. 25. 2011.
Aldactone PI as of Oct. 22, 2014, 012151s072lbl.
Kaukonen et al., Int. J. Pharmaceutics (1997) 159(2): 159-170.
Stojanovic, Technics 67, (2012).
International Search Report & Written Opinion Issued in PCT Patent Application No. PCT/US2016/059483, dated Jan. 17, 2017, 13 Pages.

* cited by examiner

*Primary Examiner* — Kendra D Carter
(74) *Attorney, Agent, or Firm* — Daniel R. Evans

(57) ABSTRACT

Disclosed herein is a pharmaceutical composition, comprising: (a) spironolactone; (b) a xanthan gum; (c) an antifoaming agent; (d) a preservative; (f) a dispersing agent; (g) a sweetening agent; (h) a flavoring agent; (i) optionally a buffer to maintain the pH of the pharmaceutical composition within a range described herein; and (j) a sufficient amount of a water vehicle.

27 Claims, 3 Drawing Sheets

SPIRONOLACTONE AQUEOUS FORMULATIONS

RELATED APPLICATION

The present application claims priority to U.S. Provisional Patent Application No. 62/495,583, filed on Oct. 30, 2015.

FIELD OF THE INVENTION

Spironolactone aqueous compositions are described herein, as well as a method of manufacture and of use thereof.

BACKGROUND OF THE INVENTION

Spironolactone (CAS Registry No. 52-01-7) is commercially available as tablets (e.g., ALDACTONE®). Spironolactone is an aldosterone antagonist having utility as a potassium sparing diuretic. (ALDACTONE® (spironolactone) Tablet Prescribing Information, as of Oct. 22, 2014.) Spironolactone is used to diagnose or treat conditions in which a person has elevated levels of aldosterone. Aldosterone is a hormone produced by the adrenal glands to help regulate the salt and water balance in the body. Spironolactone is employed in the management of primary hyperaldosteronism and the treatment of congestive heart failure. Spironolactone is also indicated for the treatment of a variety of skin disorders such as acne, hirsutism, androgenic alopecia, and rosacea. Spironolactone may also be used to treat cirrhosis of the liver, nephrotic syndrome, and essential hypertension. Spironolactone, when added to a standard therapy for adults with severe heart failure, has been shown to result in a 30% reduction in mortality. (M. L. Buck, *The Annals of Pharmacotherapy* (2005) 39(5): 823-828.) Additionally, spironolactone has become a standard part of combination diuretic regimens in infants with chronic lung disease and children with heart disease. (M. L. Buck, *The Annals of Pharmacotherapy* (2005) 39(5): 823-828.) Oftentimes tablet administration is not possible, especially for the above-mentioned adult patients with severe heart failure or with the pediatric patients.

As there is presently no commercial available aqueous-based spironolactone drug product, a physician, in the clinical setting, must rely on the pharmacy to prepare a compounded spironolactone formulation. The pharmacist, in turn, typically prepares the compounded spironolactone formulation from the commercially available tablet or from powder spironolactone. Compounded formulations may be problematic for pharmacists because of the potential for microbial contamination. Compounded formulations may be problematic for the physician, and importantly, the patient, due to the potential errors associated with compounding. Further, the stability of the compounded formulations is oftentimes unknown. As related to spironolactone, the literature includes reports by others that examine the stability of spironolactone in compounded formulations.

Gupta et al., *American Journal of Hospital Pharmacy* (1978), 35(11): 1382-1385 examines the stability of spironolactone in a compounded spironolactone formulation comprised of a simple syrup vehicle containing 10% alcohol and 0.1% sodium benzoate used as a preservative. Therein, Gupta et al. reports that the compounded spironolactone formulation having a pH of 6.2 retains 97.4% of the initial spironolactone after 160 days. Gupta et al. explains that the compounded spironolactone formulations described therein have limited stability but can be used by pharmacists extemporaneously on an as-needed basis. Gupta et al. mentions that the bioavailability of the compounded spironolactone formulation was not examined.

Mathur et al., *American Journal of Hospital Pharmacy* (1989) 46(10): 2040-2042 report that compounded spironolactone formulations were prepared by grinding commercially available film-coated spironolactone tablets, adding Purified Water, USP to the ground material followed by triturating that composition to form a paste, and then suspending the paste in Cherry Syrup, NF. Mathur et al. describe the stability of spironolactone in three compounded spironolactone formulations with theoretical concentrations of 2.5 mg/mL, 5.0 mg/mL, and 10.0 mg/mL. Mathur et al. also describe an HPLC assay for determining the spironolactone content over a period of time. Therein, Mathur et al. examine the concentrations of spironolactone remaining for the three compounded spironolactone formulations at various temperatures that range from 5° C. to 30° C. Based on the HPLC assay results, Mathur et al. state that compounded spironolactone formulations at the stated concentrations exhibited less than 5% degradation after four weeks of storage. Mathur et al. also state that microbial evaluation by the USP antimicrobial preservatives effective test showed that the samples exhibited bacterial and fungal counts well within acceptable limits.

Pramar et al., *Journal of Clinical Pharmacy and Therapeutics* (1992): 17(4): 245-248 report the development of a stable oral liquid dosage form of spironolactone. As a part of that study, Pramar et al. mention that a clear and stable oral liquid dosage form of spironolactone is not available because the aqueous solubility of spironolactone is reported to be only 28 µg/mL. Pramar et al. describe ten different spironolactone-containing liquid dosage forms with spironolactone present at a concentration of 0.2% w/v in a vehicle comprised mainly of polyethylene glycol 400 (30% v/v) and mono- and polyhydric alcohols (ethanol (10% v/v), propylene glycol (10% v/v), and glycerin (10% v/v)). Pramar et al. mention that the amounts of propylene glycol and polyethylene glycol 400 alone were too high in order to achieve a spironolactone concentration of 2 mg/mL (i.e., 0.2% w/v). For instance, Pramar et al. explains that propylene glycol, when administered in high doses, is known to cause lactic acidosis in children. Pramar et al. identify a particular dosage form (i.e., Formulation C), as being stable based on accelerated testing at 40° C. and a relative humidity of 75%. Interestingly, the reported dosage forms also include phosphate or citrate buffer (50 mM) adjusted to a final pH of 4.5, in which the reported final pH is identified therein as being the pH at which spironolactone exhibits maximum stability. Pramar et al. *Drug Development and Industrial Pharmacy* (1991) 17(5): 747-761; Pramar et al. Journal of Pharmaceutical Sciences (1991) 80(6): 551-553. As related to the dosage form containing citrate, Pramar et al. mention that a spironolactone-containing liquid dosage form including citrate buffer (i.e., Formulation B) is unsuitable because of the resultant instability.

Nahata et al., *The Annals of Pharmacotherapy* (1993) 27(10): 1198-1199 report that a compounded spironolactone formulation prepared from tablets exhibits stability for three months. Nahata et al. criticizes the dosage forms described in the aforementioned Pramar et al. reference as being unsuitable for certain patients (e.g., infants) due to the high concentrations of propylene glycol and ethanol. The compounded spironolactone formulation of Nahata et al. contains carboxymethylcellulose as a suspending agent, "which may provide uniform doses by minimizing settling of the drug in the bottle during use by patients." Despite the presence of the carboxymethylcellulose suspending agent, Nahata et al. observe variability in concentration assay measurements that "was most likely attributable to sampling of nonuniform dispersion of drug particles in the suspension."

U.S. Pat. No. 4,837,211 to J. L. Olsen, describes a spironolactone-containing composition that purports to overcome the uniformity issue by utilizing sodium carboxymethylcellulose or a mixture of methylcellulose and a dimethylpolysiloxane polymer. It was discovered that a spironolactone-containing composition comparable to the composition described in Example V resulted in an increase in sedimentation and that uniformity could only be achieved after vigorous shaking for 60-120 seconds after storage at 25±2° C. and 40±5% relative humidity. The extended time required to resuspend spironolactone in the composition is problematic in that it may result in reduced patient compliance—especially for an elderly patient. Further, administration errors may arise if the spironolactone is not uniformly dispersed throughout the composition.

Additional reports describe compounded spironolactone formulations as having a shelf-life stability of either 60 days (Allen et al., *American Journal of Health-System Pharmacy* (1996) 53(19): 2304-2309) or 90 days (BasuSarkar et al. International Journal of Pharmaceutical Review and Research (2013) 23(1): 67-70). However, these additional reports do not consider the uniformity of the compounded suspension.

Kaukonen et al., *Journal of Pharmacy and Pharmacology* (1998) 50(6): 611-619 recognize the drawbacks associated with the above-mentioned compounded spironolactone formulations and the spironolactone-containing liquid dosage forms. In an effort to overcome those drawbacks Kaukonen et al. describe an oral solution of spironolactone containing water-soluble derivatives of β-cyclodextrin (e.g., sulfobutyl ether β-cyclodextrin (SBE7) or dimethyl-β-cyclodextrin (DM-β-CyD)). Therein, Kaukonen et al. conducted a comparative evaluation of selected pharmacokinetic parameters of oral solutions containing spironolactone and either SBE7 or DM-β-CyD versus a compounded spironolactone formulation. Kaukenen et al. state that oral bioavailability of the oral solutions is about three times greater than the compounded spironolactone formulation. A potential drawback to the oral solution described by Kaukonen et al. is the differences in bioavailability, which would require a clinician to estimate the dosage amounts for a given subject, and thus lead to potential dosing errors.

In view of the foregoing, there is a need for a spironolactone aqueous composition that is ready to use having acceptable long-term stability and resuspension properties that contribute to patient compliance and reduce the likelihood of dosing errors.

SUMMARY OF THE INVENTION

Disclosed herein is a pharmaceutical composition, comprising: (a) spironolactone; (b) a xanthan gum; (c) an anti-foaming agent; (d) a preservative; (f) a dispersing agent; (g) a sweetening agent; (h) a flavoring agent; (i) optionally a buffer to maintain the pH of the pharmaceutical composition within a range described herein; and (j) a sufficient amount of a water vehicle.

DEFINITIONS

Figure 1:
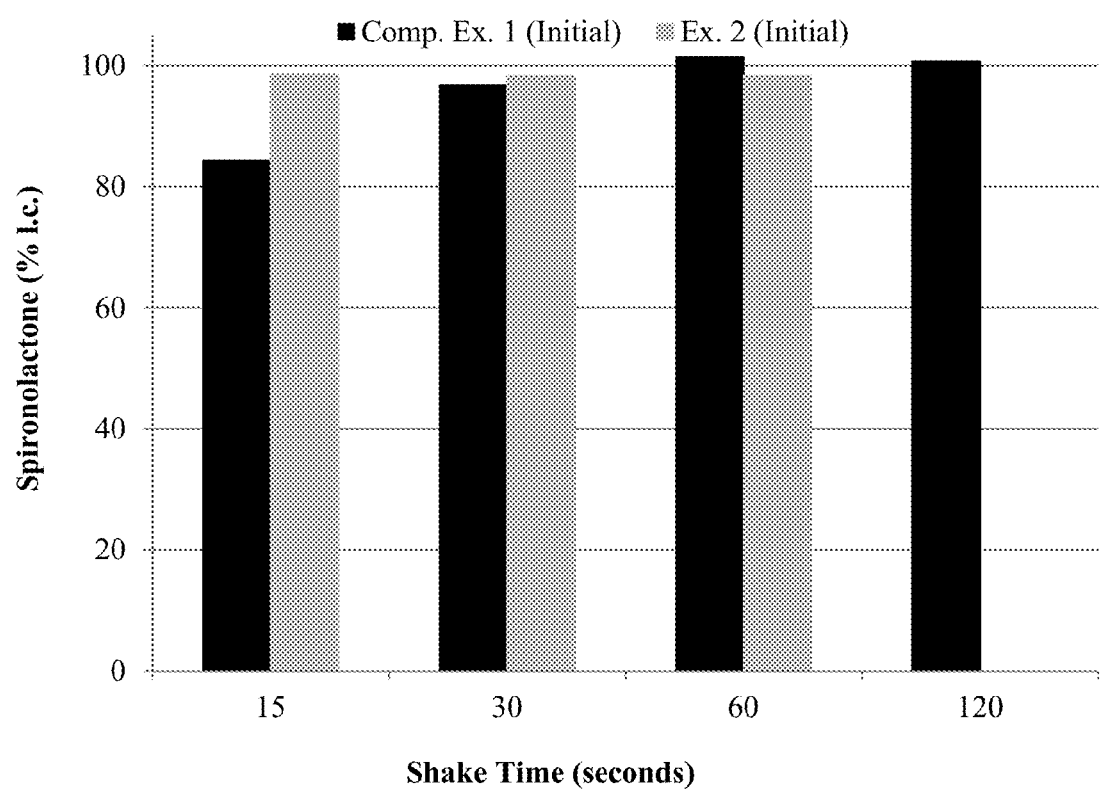
FIG. 1 shows the initially observed spironolactone content (% l.c.) as a function of shake-time (in seconds) for the compositions of Example 2 (grey bars) and Comparative Example 1 (black bars).

The term "about" has its customary meaning, as defined in the USP, Section 8.20, which states that "about" indicates a quantity within 10%.

A stated amount for a compositional ingredient that is not preceded by the term "about" does not mean that there is no variance for the stated term, as one of ordinary skill would understand that there is always some possibility of a degree of variability generally associated with experimental error.

The concentration unit "% w/v" is a measure of the weight amount of a specified ingredient based on the total volume of the composition.

As used herein, long-term storage conditions refers to storing a sample for a designated time at 25±2° C. and 40±5% relative humidity ("RH"). For simplicity, "long-term storage conditions," is abbreviated as "long-term storage" or "long-term."

As used herein, accelerated storage conditions refers to storing a sample for a designated time at 40±2° C. and not more than 25% RH (i.e., <25% RH). For simplicity, "accelerated storage conditions," is abbreviated as "accelerated storage" or "accelerated."

DETAILED DESCRIPTION

Disclosed herein is a pharmaceutical composition, comprising: (a) spironolactone; (b) a xanthan gum; (c) an anti-foaming agent; (d) a preservative; (e) a dispersing agent; (f) a sweetening agent; (g) a flavoring agent; (h) optionally a buffer to maintain the pH of the pharmaceutical composition within a defined range; and (i) a sufficient amount of a water vehicle.

The spironolactone may be present in an amount that ranges from 0.20% w/v to 1.0% w/v and all amounts in between, including, for example 0.3% w/v, 0.4% w/v, 0.5% w/v, 0.6% w/v, 0.7% w/v, 0.8% w/v, and 0.9% w/v. In a particular embodiment, spironolactone is present in an amount of 0.5% w/v.

The xanthan gum may be present in an amount that ranges from 0.18% w/v to 0.36% w/v and all amounts in between, including, for example, 0.19% w/v, 0.20% w/v, 0.21% w/v, 0.22% w/v, 0.23% w/v, 0.24% w/v, 0.25% w/v, 0.26% w/v, 0.27% w/v, 0.28% w/v, 0.29% w/v, 0.30% w/v, 0.31% w/v, 0.32% w/v, 0.33% w/v, 0.34% w/v, 0.35% w/v. In a particular embodiment, xanthan gum is present in an amount of 0.25% w/v.

The anti-foaming agent aids in the removal of air, such as entrapped air, from the pharmaceutical compositions described herein. Simethicone emulsion is an example of an anti-foaming agent. The simethicone emulsion may be present in an amount that ranges from 0.1% w/v to 0.6% w/v, and all amounts in between, including, for example, 0.2% w/v, 0.3% w/v, 0.4% w/v, 0.5% w/v. In a particular embodiment, simethicone emulsion is present in an amount of 0.2% w/v.

The preservative aids in the preservation of the compositions described herein against certain microbial organisms, including one or more of *E. coli, P. aeruginosa, S. aureus, A. brasiliensis, B. cepacia,* and *C. albicans*. Preservatives contemplated herein include methylparaben or propylparaben and the salts thereof (e.g., sodium, potassium, etc.), sodium benzoate, citric acid, benzoic acid, butylated hydroxytoluene, and butylated hydroxyanisole, sorbic acid, and a sorbate salt (e.g., sodium, potassium, ammonium, calcium, etc.) and the mixtures thereof). In a particular embodiment, the preservative is comprised of sorbic acid and a sorbate salt (e.g., sodium, potassium, ammonium, calcium, etc.). The amount of sorbic acid includes 0.025% w/v to 0.050% w/v, while the amount of sorbate salt includes 0.10% w/v to 0.20% w/v. In another particular embodiment, the preservative is comprised of 0.025% w/v to 0.050% w/v of sorbic acid and 0.10% w/v to 0.20% w/v of potassium sorbate, and in yet another embodiment, the preservative is comprised of 0.050% w/v of sorbic acid and 0.20% w/v of potassium sorbate. One of ordinary skill will appreciate that the equilibrium pKa-value of sorbic acid and sorbate is about 4.8. Accordingly, the molar amounts of sorbic acid and sorbate in the pharmaceutical composition described herein depend on the pH of the composition. Therefore, one of ordinary skill would appreciate that the amount of sorbate (i.e., sorbic acid and potassium sorbate) in the pharmaceutical composition refers to the amount added during manufacture.

The dispersing agent aids in dispersing spironolactone in the pharmaceutical compositions described herein. Contemplated dispersing agents, include, for example, propylene glycol, glycerin, or a mixture thereof. In a particular embodiment the dispersing agent is glycerin. In another embodiment, the pharmaceutical composition comprises from 1.8% w/v to 2.4% w/v glycerin, and all amounts in between, including, for example, 1.9% w/v, 2.0% w/v, 2.1% w/v, 2.2% w/v, and 2.3% w/v. Specifically contemplated amounts range from 1.9% w/v to 2.3% w/v glycerin, from 2.0% w/v to 2.2% w/v, or from 2.1% w/v to 2.2% w/v glycerin.

The sweetening agent aids in the palatability of the pharmaceutical compositions described herein. Contemplated sweetening agents, include, for example, sucralose, ammonium glycyrrhizinate, acesulfame-K, aspartame, saccharin, a saccharin salt (e.g., sodium, potassium, calcium, etc.), sodium cyclamate, and mixtures thereof. The amount of sweetener can vary according to the desired sweetness and that amount of sweetening agent depends at least in part on the amount of spironolactone. The percentage amount of the sweetening agent contained in a pharmaceutical composition described herein ranges from 0.005% w/v to 10% w/v, from 0.05% w/v to 5% w/v, or from 0.1% to 1% (w/v). In a particular embodiment, the sweetening agent comprises from about 0.04% w/v to 0.6% w/v (more particularly 0.14% w/v) sodium saccharin and from 0.03% w/v to 0.04% w/v ammonium glycyrrhizinate, based on the content of glycyrrhizic acid.

The flavoring agent likewise aids in the palatability of the pharmaceutical compositions described herein. Contemplated flavoring agents include, e.g., cherry, orange, banana, strawberry or other acceptable fruit flavors, or mixtures of cherry, orange, and other acceptable fruit flavors. The amount of flavoring agent can range, for example, from 0.1% w/v to 0.5% w/v. In a particular embodiment, the flavoring agent comprises a banana flavor in the amount of 0.3% w/v.

The buffer, when present, serves to maintain the pH of the pharmaceutical compositions described herein within a defined range. Suitable buffers include those buffers described in, for example, G. L. Flynn, "Buffers—pH Control within Pharmaceutical Systems," J. Parenteral Drug Assoc. (1980) 34(2): 139-162. A suitable buffer is one that is not only capable of maintaining a pH that ranges from 4.5 to 5.5, but also be compatible with the pharmaceutical composition described herein. Suitable contemplated buffers included, for example, acetate, aconitate, glutarate, glutamate, malate, succinate, tartrate, citrate, and phosphate. A specifically contemplated buffer is comprised of citric acid, monobasic citrate, dibasic citrate, and tribasic citrate, in which the mono-, di-, or tribasic citrate forms have associated counterions, and thus, may collectively be referred to as citrate salts, or in particular, a citrate salt. The associated counterions include, for example, sodium, potassium, ammonium, calcium, etc. For instance, a particular citrate salt contemplated herein is sodium citrate, which may exist as a hydrated form, such as, a dihydrate or a pentahydrate. In a particular embodiment, the buffer molar concentration ranges from about 10 mM to about 100 mM, which corresponds to a buffer comprised of 0.07% w/v to 0.0.7% w/v citric acid and 0.18% w/v to 1.86% w/v of a citrate salt. One of ordinary skill will appreciate that the buffer concentration can be any numerical value between about 10 mM to about 100 mM, including for example, 15 mM, 20 mM, 25 mM, 30 mM, 35, mM, 45 mM, 50 mM, 55 mM, 60 mM, 65 mM, 70 mM, 75 mM, 80 mM, 85 mM, 90 mM and 95 mM. In another embodiment, the buffer is comprised of 0.20% w/v citric acid and 0.43% w/v sodium citrate dihydrate. One of ordinary skill will understand that the molar amounts of citric acid and sodium citrate, relative to each other, will depend on the pH of the composition. Therefore, one of ordinary skill would appreciate that the amount of citrate (i.e., citric acid and sodium citrate) in the pharmaceutical composition refer to the amount added during manufacture. In a particular embodiment, the pH of the pharmaceutical composition ranges from about 4.5 to about 5.5, from about 4.8 to about 5.5, from about 4.8 to about 5.4, from about 4.8 to about 5.3, or from about 4.8 to about 5.0.

The pharmaceutical compositions described herein have an acceptable viscosity that ranges from 100 cP to 300 cP, and all amounts in between, including, for example, 110 cP, 120 cP, 130 cP, 140 cP, 150 cP, 160 cP, 170 cP, 180 cP, 190 cP, 200 cP, 210 cP, 220 cP, 230 cP, 240 cP, 250 cP, 260 cP, 270 cP, 280 cP, and 290 cP. In a particular embodiment, the viscosity of the pharmaceutical composition ranges from 130 cP to 170 cP.

Pharmaceutical compositions described herein are stable when stored in a closed container, as evidenced by, for example, the amount of spironolactone being 100.0±10.0% of labeled content ("l.c."). Data shows that pharmaceutical compositions described herein have a spironolactone content that is 100±10% l.c. when stored under long-term conditions for 12-months regardless whether the container is stored in an upright position or on its side. Data also shows that pharmaceutical compositions described herein have a spironolactone content that is 100±10% l.c. when stored under accelerated conditions for 6-months regardless whether the container is stored in an upright position or on its side. It was projected that pharmaceutical compositions described herein have a spironolactone content of 100±10% l.c. for at least 24-months, and in other instances of at least for at least 36-months. The stability may also be measured by the amount of canrenone detected after long-term storage. For instance, pharmaceutical compositions described herein have an amount of canrenone that is: ≤2.0% after 24-months, ≤1.0% after 24-months, ≤0.5% after 24-months, or ≤0.3% after 24-months after long-term storage.

It is contemplated that the pharmaceutical compositions described herein are stored in a polyethylene terephthalate (PETE) bottle. In a particular embodiment, the PETE bottle is amber. In another embodiment, the amber PETE bottle is enclosed using a suitable closure. In yet another embodiment, the enclosed, amber PETE bottle has a volume of 4 oz. or 16 oz. Prior to dispensing the pharmaceutical composition to an amber PETE bottle, it may be desirable to purge with an inert gas, such as, nitrogen, and evacuate said bottle under reduced pressure. It may also be desirable to introduce an inert gas, such as, nitrogen, into the headspace of the bottle once it is filled with the pharmaceutical composition.

It was discovered that spironolactone resuspendability is an important consideration for pharmaceutical compositions described herein. For a dosage form containing suspended spironolactone, sedimentation can occur after storage for a period of time and that sedimentation results in a reduced level of dosage uniformity. For example, after storage for a period of time when the suspended spironolactone settles at the bottom of the container, the solution above the sediment contains a lower amount of spironolactone (based on the original label content) when compared to the originally prepared dosage form. This is especially problematic for compounded dosage forms typically prepared in the pharmacy. Oftentimes, it is difficult to resuspend the settled solid at the bottom of the container once the solid settles. If settling occurs, spironolactone dosage uniformity is unknown. This may be problematic when administration requires pouring a certain volume of the dosage form from the container. In order to deliver the appropriate dosage amount, it is critical that the spironolactone be uniformly distributed throughout the entire volume of the dosage form. Otherwise, the patient may receive a lower (or a higher) dosage amount than what is desired.

Pharmaceutical compositions described herein exhibit satisfactory dosage uniformity and are ready to use with minimal shaking, as determined by the resuspendability test described below. A satisfactory dosage uniformity is based on the original label content (l.c.) of the spironolactone contained within pharmaceutical compositions described herein. In particular, a satisfactory dosage uniformity is one where the amount of spironolactone throughout the composition is about 100% l.c. (i.e., 100±10%). A satisfactory dosage uniformity is obtained within about 10 seconds of shaking, within about 5 to about 10 seconds of shaking, and within about 5 seconds of shaking regardless of the storage conditions. That is, an amount of spironolactone of about 100% l.c. may be achieved within about 10 seconds of shaking, within about 5 to about 10 seconds of shaking, or within about 5 seconds of shaking.

A first embodiment is a pharmaceutical composition, comprising: (a) 0.50% w/v of spironolactone; (b) from 0.18% w/v to 0.36% w/v of a xanthan gum; (c) an anti-foaming agent; (d) a preservative; (e) a dispersing agent; (f) a sweetening agent; (g) a flavoring agent; (h) optionally a sufficient amount of a buffer to maintain the pH of the pharmaceutical composition from 4.5 to 5.5; and (i) a sufficient amount of a water vehicle.

In a first aspect of the pharmaceutical composition of the first embodiment, the anti-foaming agent (c) is comprised of a simethicone emulsion; the preservative (d) is comprised of sorbic acid and a sorbate salt; the dispersing agent (e) is comprised of glycerin; and the sweetening agent (f) is comprised of a sweetener selected from the group consisting of a saccharin salt, a glycyrrhizinate salt, and combinations thereof.

In a second aspect of the pharmaceutical composition of the first embodiment, the anti-foaming agent (c) is comprised of 0.20% w/v of a simethicone emulsion; the preservative (d) is comprised of from 0.025% w/v to 0.050% w/v of sorbic acid and from 0.10% w/v to 0.20% w/v of a sorbate salt; the dispersing agent (e) is comprised of (f) 1.8% w/v to 2.4% w/v glycerin; and the sweetening agent (f) is comprised of a sweetener selected from the group consisting of a saccharin salt, a glycyrrhizinate salt, and combinations thereof.

In a third aspect of the pharmaceutical composition of the first embodiment, the anti-foaming agent (c) is comprised of 0.20% w/v of a simethicone emulsion; the preservative (d) is comprised of from 0.025% w/v to 0.050% w/v of sorbic acid and from 0.10% w/v to 0.20% w/v of a sorbate salt; the dispersing agent (e) is comprised of from 1.8% w/v to 2.4% w/v glycerin; and the sweetening agent (f) comprises a saccharin (sodium, potassium, ammonium, calcium) salt and a glycyrrhizinate salt; and wherein the pharmaceutical composition comprises the buffer comprised of citric acid and a citrate salt.

In a fourth aspect of the pharmaceutical composition of the first embodiment, the anti-foaming agent (c) is comprised of 0.20% w/v of a simethicone emulsion; the preservative (d) is comprised of from 0.025% w/v to 0.050% w/v of sorbic acid and from 0.10% w/v to 0.20% w/v of potassium sorbate; the dispersing agent (e) is comprised of from 1.8% w/v to 2.4% w/v glycerin; and the sweetening agent (f) comprises sodium saccharin and ammonium glycyrrhizinate; and wherein the pharmaceutical composition comprises the buffer comprised of citric acid and a citrate salt.

In a fifth aspect of the pharmaceutical composition of the first embodiment, the anti-foaming agent (c) is comprised of 0.20% w/v of a simethicone emulsion; the preservative (d) is comprised of from 0.025% w/v to 0.050% w/v of sorbic acid and from 0.10% w/v to 0.20% w/v of potassium sorbate; the dispersing agent (e) is comprised of from 1.8% w/v to 2.4% w/v glycerin; the sweetening agent (f) comprises sodium saccharin and ammonium glycyrrhizinate; and wherein the pharmaceutical composition comprises the buffer comprised of from 0.17% w/v to 0.24% w/v citric acid and from 0.36% w/v to 0.48% w/v of a citrate salt.

In a sixth aspect of the pharmaceutical composition of the first embodiment, the anti-foaming agent (c) is comprised of 0.20% w/v of a simethicone emulsion; the preservative (d) is comprised of from 0.025% w/v to 0.050% w/v of sorbic acid and from 0.10% w/v to 0.20% w/v of potassium sorbate; the dispersing agent (e) is comprised of from 1.9% w/v to 2.3% w/v glycerin; and the sweetening agent (f) comprises 0.14% w/v sodium saccharin and from 0.03% w/v to 0.04% w/v ammonium glycyrrhizinate; and wherein the pharmaceutical composition comprises the buffer comprised of from 0.17% w/v to 0.24% w/v citric acid and from 0.36% w/v to 0.48% w/v of a citrate salt.

In a seventh aspect of the pharmaceutical composition of the first embodiment, the anti-foaming agent (c) is comprised of 0.20% w/v of a simethicone emulsion; the preservative (d) is comprised of 0.050% w/v of sorbic acid and 0.20% w/v of potassium sorbate; the dispersing agent (e) is comprised of from 2.0% w/v to 2.2% w/v glycerin; and the sweetening agent (f) comprises 0.14% w/v sodium saccharin and from 0.03% w/v to 0.04% w/v ammonium glycyrrhizinate; and wherein the pharmaceutical composition comprises the buffer comprised of from 0.17% w/v to 0.24% w/v citric acid and from 0.36% w/v to 0.48% w/v of a citrate salt.

In an eighth aspect of the pharmaceutical composition of first embodiment, the viscosity ranges from 100 cP to 300 cP. It was discovered that the viscosity of pharmaceutical compositions described herein is an important consideration. For instance, a viscosity less than 100 cP may be problematic with respect to the resuspendability of the pharmaceutical composition. Not to be bound by theory, it is believed that a viscosity less than 100 cP promotes sedimentation. Further, a viscosity greater than 300 cP results in a solution that is too viscous, which may be problematic with respect to product dispensation, i.e., the solution may become too thick to dispense easily.

In a ninth aspect of the pharmaceutical composition of the first embodiment, the anti-foaming agent (c) is comprised of 0.20% w/v of a simethicone emulsion; the preservative (d) is comprised of 0.050% w/v of sorbic acid and 0.20% w/v of potassium sorbate; the dispersing agent (e) is comprised of from 2.1% w/v to 2.2% w/v glycerin; the sweetening agent (f) comprises 0.14% w/v sodium saccharin and from 0.03% w/v to 0.04% w/v ammonium glycyrrhizinate; and wherein the pharmaceutical composition comprises the buffer comprised of 0.20% w/v citric acid and 0.43% w/v sodium citrate.

In a tenth aspect of the pharmaceutical composition of the first embodiment, xanthan gum is present in an amount of 0.25% w/v; the anti-foaming agent (c) is comprised of 0.20% w/v of a simethicone emulsion; the preservative (d) is comprised of 0.050% w/v of sorbic acid and 0.20% w/v of potassium sorbate; the dispersing agent (e) is comprised of from 2.1% w/v to 2.2% w/v glycerin; the sweetening agent (f) comprises 0.14% w/v sodium saccharin and from 0.03% w/v to 0.04% w/v ammonium glycyrrhizinate; and wherein the pharmaceutical composition comprises the buffer comprised of 0.20% w/v citric acid and 0.43% w/v sodium citrate.

In an eleventh aspect of the pharmaceutical composition of the first embodiment, xanthan gum is present in an amount of 0.25% w/v; the anti-foaming agent (c) is comprised of 0.20% w/v of a simethicone emulsion; the preservative (d) is comprised of 0.050% w/v of sorbic acid and 0.20% w/v of potassium sorbate; the dispersing agent (e) is comprised of from 2.1% w/v to 2.2% w/v glycerin; the sweetening agent (f) comprises 0.14% w/v sodium saccharin and from 0.03% w/v to 0.04% w/v ammonium glycyrrhizinate; and wherein the pharmaceutical composition comprises the buffer comprised of 0.20% w/v citric acid and 0.43% w/v sodium citrate and the viscosity of the composition ranges from 130 cP to 170 cP.

In a twelfth aspect of the pharmaceutical composition of the first embodiment, xanthan gum is present in an amount of 0.25% w/v; the anti-foaming agent (c) is comprised of 0.20% w/v of a simethicone emulsion; the preservative (d) is comprised of 0.050% w/v of sorbic acid and 0.20% w/v of potassium sorbate; the dispersing agent (e) is comprised of from 2.1% w/v to 2.2% w/v glycerin; the sweetening agent (f) comprises 0.14% w/v sodium saccharin and from 0.03% w/v to 0.04% w/v ammonium glycyrrhizinate; and wherein the pharmaceutical composition comprises the buffer comprised of 0.20% w/v citric acid and 0.43% w/v sodium citrate, and the viscosity of the composition ranges from 130 cP to 170 cP, and the pH of the pharmaceutical composition ranges from about 4.5 to about 5.5.

A thirteenth aspect of the pharmaceutical composition of the first embodiment is directed to an enclosed, amber polyethylene terephthalate (PETE) bottle comprising the pharmaceutical composition of the first embodiment.

A fourteenth aspect of the pharmaceutical composition of the first embodiment is directed to an enclosed, amber polyethylene terephthalate (PETE) bottle comprising the pharmaceutical composition of the first embodiment, wherein the volume of said bottle is 4 oz. (about 118 mL) or 16 oz (about 473 mL).

In a fifteenth aspect of the pharmaceutical composition of the first embodiment, the shake time to achieve a uniform amount (i.e., about 100% l.c.) of spironolactone occurs within about 10 seconds.

In a sixteenth aspect of the pharmaceutical composition of the first embodiment, the shake time to achieve a uniform amount (i.e., about 100% l.c.) of spironolactone occurs within about 5 to about 10 seconds.

In a seventeenth aspect of the pharmaceutical composition of the first embodiment, the shake time to achieve a uniform amount (i.e., about 100% l.c.) of spironolactone occurs within about 5 seconds.

A second embodiment is directed to a pharmaceutical composition comprising: (a) 0.50% w/v spironolactone; (b) 0.25% w/v of a xanthan gum; (c) 0.20% w/v of a simethicone emulsion; (d) a preservative comprised of 0.050% w/v of sorbic acid and 0.20% w/v of potassium sorbate; (e) from 2.1% w/v to 2.2% w/v glycerin; (f) a sweetening agent containing 0.14% w/v sodium saccharin and from 0.03% w/v to 0.04% w/v ammonium glycyrrhizinate; (g) 0.30% w/v of a fruit flavoring agent; (h) a buffer comprised of 0.20% w/v citric acid and 0.43% w/v sodium citrate; and (i) a sufficient amount of a water vehicle.

In a first aspect of the pharmaceutical composition of the second embodiment, the pharmaceutical composition has a pH of from 4.5 to 5.5.

In a second aspect of the pharmaceutical composition of the second embodiment, the pharmaceutical composition has a pH of from 4.8 to 5.2.

In a third aspect of the pharmaceutical composition of the second embodiment, the pharmaceutical composition has a viscosity that ranges from 100 cP to 300 cP.

In a fourth aspect of the pharmaceutical composition of the second embodiment, the pharmaceutical composition has a viscosity that ranges from 100 cP to 300 cP.

In a fourth aspect of the pharmaceutical composition of the second embodiment, the pharmaceutical composition has a viscosity that ranges from 130 cP to 170 cP.

A fifth aspect of the pharmaceutical composition of the second embodiment is directed to an enclosed, amber polyethylene terephthalate (PETE) bottle comprising the pharmaceutical composition of the first embodiment.

A sixth aspect of the pharmaceutical composition of the second embodiment is directed to an enclosed, amber polyethylene terephthalate (PETE) bottle comprising the pharmaceutical composition of the second embodiment, wherein the volume of said bottle is 4 oz. (about 118 mL) or 16 oz (about 473 mL).

In a seventh aspect of the pharmaceutical composition of the second embodiment, the shake time to achieve a uniform amount (i.e., about 100% l.c.) of spironolactone occurs within about 10 seconds.

In an eight aspect of the pharmaceutical composition of the second embodiment, the shake time to achieve a uniform amount (i.e., about 100% l.c.) of spironolactone occurs within about 5 to about 10 seconds.

In a ninth aspect of the pharmaceutical composition of the second embodiment, the shake time to achieve a uniform amount (i.e., about 100% l.c.) of spironolactone occurs within about 5 seconds.

A third embodiment is directed to a process for preparing the pharmaceutical composition of the first embodiment, which comprises: (1) mixing the xanthan gum, anti-foaming agent, preservative, a portion of the sweetening agent, and, optionally, the buffer, in water in a first container; (2) mixing the spironolactone, the dispersing agent, and the remaining portion of the sweetening agent in a second container; (3) transferring the contents of the second container to the first container followed by mixing the contents of the first container; (4) adding the flavoring agent to the contents of the first container from step (3); (5) adding water to the first container of step (3) and mixing the contents of the first container; (6) optionally, adding a sufficient amount of buffer to the first container to maintain the pH of the composition from 4.8 to 5.0; and (7) dispensing the contents of the first container from step (5) or the contents of the first container into an amber polyethylene terephthalate bottle.

A first aspect of the third embodiment is directed to a pharmaceutical product prepared by the process of the third embodiment.

A second aspect of the third embodiment is directed to a pharmaceutical product prepared by any one of the exemplified embodiments described herein.

According to the above-mentioned ALDACTONE® (spironolactone) Tablet Prescribing Information, ALDACTONE® (spironolactone) is indicated: (i) in the management of primary hyperaldosteronism; (ii) in the short-term preoperative treatment of patients with primary hyperaldosteronism; (iii) in the long-term maintenance therapy for patients with discrete aldosterone-producing adrenal adenomas who are judged to be poor operative risks or who decline surgery; and (iv) in the long-term maintenance therapy for patients with bilateral micro or macronodular adrenal hyperplasia (idiopathic hyperaldosteronism).

ALDACTONE® (spironolactone) is also indicated for edematous conditions for patients with congestive heart failure, for the management of edema and sodium retention when the patient is only partially responsive to, or is intolerant of, other therapeutic measures. ALDACTONE® is further indicated for patients with congestive heart failure taking *digitalis* when other therapies are considered inappropriate.

ALDACTONE® (spironolactone) is also indicated for the treatment of hypertension, to lower blood pressure; for the treatment of patients with hypokalemia when other measures are considered inappropriate or inadequate. ALDACTONE® is also indicated for the prophylaxis of hypokalemia in patients taking digitalis when other measures are considered inadequate or inappropriate.

ALDACTONE® (spironolactone) is also indicated for the treatment of severe heart failure (NYHA class III-IV), so as to increase survival, and to reduce the need for hospitalization for heart failure when used in addition to standard therapy.

One of ordinary skill would understand that the pharmaceutical compositions described herein are useful for the indications associated with the ALDACTONE® drug product. One of ordinary skill would also be able to consult the ALDACTONE® prescribing information or rely on sound judgment so as to ascertain a therapeutically effective amount of the pharmaceutical compositions described herein.

A fourth embodiment is directed to a method for the treatment of a patient in need thereof in a manner consistent with any one of the approved indications associated with ALDACTONE®, which comprises administering to the subject a therapeutically effective amount of the pharmaceutical composition of the first or second embodiment.

A fifth embodiment is directed to a method for the treatment of hypertension in a subject in need thereof, which comprises administering to the subject a therapeutically effective amount of the pharmaceutical composition of the first or second embodiment.

In a first aspect of the fifth embodiment, the composition is administered orally or by a nasogastric tube.

A sixth embodiment is directed to a method for the treatment of severe heart failure in a subject in need thereof, which comprises administering to the subject a therapeutically effective amount of the pharmaceutical composition of the first or second embodiment; wherein the composition is administered orally or by a nasogastric tube.

A seventh embodiment is directed to a method for the treatment of a patient suffering from a skin disorder, which comprises administering to the subject a therapeutically effective amount of the pharmaceutical composition of the first or second embodiment, wherein said skin disorder is selected from the group consisting of acne, hirsutism, androgenic alopecia, rosacea, and combinations thereof.

EXAMPLES

Spironolactone is commercially available as a micronized or unmicronized solid. The median (volume) particle size of commercially available unmicronized spironolactone was 7.47 µm, 18.3 µm, and 35.5 µm for D(v,0.1), D(v,0.5), and D(v,0.9), respectively. The manufacturer's specifications for the micronized spironolactone is <10 µm (not less than 90.0%) and <25 µm (not less than 99.0%). The micronized spironolactone used in the examples described herein, e.g., Example 2, had a particle size of about 0.42 µm, about 3.64 µm, and about 9.42 µm, for D(v,0.1), D(v,0.5), and D(v,0.9), respectively. A dissolution profile for unmicronized spironolactone was slower compared to micronized spironolactone. For instance, in a dissolution study done in a manner consistent with USP <711>, the unmicronized spironolactone at 5-minutes resulted in about 50% of labeled content dissolved, while at the same time the micronized spironolactone resulted in about 90% of labeled content dissolved. Accordingly, in the exemplified embodiments that follow, spironolactone refers to micronized spironolactone.

Xanthan gum (i.e., Xanthan Gum, NF) is a water soluble hydrocolloid that acts as the suspending agent in the composition by increasing the viscosity of the continuous (aqueous) phase which reduces sedimentation. Xanthan gum is commercially available, used as purchased, and complies with USP-NF requirements.

Simethicone Emulsion is used as an anti-foaming agent in the compositions described herein. It is a water-dilutable, non-ionic emulsion containing about 30% simethicone, about 1-5% silica gel, about 1-5% polyethylene glycol stearate, and water. Simethicone Emulsion is commercially available, used as purchased, and complies with USP-NF requirements.

Sorbic acid is an antimicrobial preservative. Sorbic Acid is commercially available, used as purchased, and complies with USP-NF requirements.

Potassium Sorbate is an antimicrobial preservative. Potassium Sorbate is commercially available, used as purchased, and complies with USP-NF requirements.

Saccharin sodium is a sweetening agent used to improve the palatability of the compositions described herein. Saccharin Sodium is commercially available, used as purchased, complies with USP-NF requirements.

Citric Acid is a pH modifier (buffering agent) used to maintain the composition pH from about 4.5 to about 5.5. Citric Acid is commercially available, used as purchased, and complies with USP-NF requirements.

Sodium Citrate Dihydrate is a pH modifier (buffering agent) used to maintain the composition pH of about 4.5 to about 5.5. Sodium Citrate Dihydrate is commercially available, used as purchased, and complies with USP-NF requirements. One of ordinary skill would recognize that other forms of citrate may be used in the compositions described herein.

Magnasweet 110 (i.e., sweetener) is a sweetening agent used for masking after-tastes and enhancing sweetness. Magnasweet 110 contains from 8.5 to 10% w/w monoammonium glycyrrhizinate, as measured by the content of glycyrrhizic acid, in a glycerin vehicle having a specific gravity of about 1.27. A typical amount of monoammonium glycyrrhizinate, as measured by the content of glycyrrhizic acid, found in Magnasweet 110 is about 9.9% w/w. Magnasweet 110 is commercially available and used as purchased.

Glycerin is used as a dispersing agent for the spironolactone. Glycerin is commercially available, used as purchased, and complies with USP-NF requirements.

Artificial banana flavor (i.e., fruit flavor) is a flavor used to improve the palatability of the composition. In addition to the flavoring substances, artificial banana flavor contains a vehicle comprised of propylene glycol (70-80%), water (5-15%), and ethyl alcohol (1-10%). Artificial banana flavor is commercially available and used as purchased.

Purified water, which meets USP-NF requirements, is used as the primary solvent for the excipients and diluent for the compositions described herein.

Specific gravity was measured in a manner consistent with USP <841>, Method I, using a calibrated pycnometer at a temperature of 25° C. being careful to exclude foam and air bubbles.

Dosage uniformity was measured in a manner consistent with USP <905>.

Dissolution was measured in a manner consistent with USP <711> reporting the amount of dissolved spironolactone as a percent of labeled content with an associated relative standard devision ("RSD").

Amounts of spironolactone, related impurities (e.g., canrenone and β-spironolactone), and sorbate were determined by HPLC.

Resuspendability tests for a given sample stored under long-term and accelerated conditions. Analysis of samples is performed using a nominal concentration of about 0.50 mg/ml spironolactone. The following procedure was employed for the resuspendability test: (1) Shake pharmaceutical composition (spironolactone concentration of 5.0 mg/mL) composition thoroughly for 5 seconds, 10 seconds and 15 seconds. Invert the bottle to aid in mixing. (Additional time points may be added if necessary). Note: shake times are cumulative. Therefore, after the first shake of 5 seconds a sample aliquot is withdrawn (5 second sample), then the sample is shaken for an additional 5 seconds to obtain a 10 second aliquot and so on. (2) Transfer approximately 5.0 mL of suspension after each shake time, accurately weighed, to a 50-mL volumetric flask. (3) Dilute to volume with Diluent and mix well. (4) Filter a portion of the sample through a filter (Whatman 0.45 µm Nylon with glass microfiber (GMF) or equivalent) discarding at least the first 2 mLs.

Samples were assayed by HPLC using a Waters Sunfire C-18, 10 um, 4.6 mm×150 mm column (or its equivalent) operating at a column temperature of 40° C. (sample Temperature: Ambient) with a mobile phase comprised of 50:50% v/v acetonitrile:water operating at a flow rate of 1.0 mL/min and an injection volume of 5 µL. Spironolactone elutes with an approximate retention time of about 7.5 min and the chromatogram peak is detected using ultraviolet light at a wavelength of 238 nM (Attenuation: 1 AUFS). A typical chromatogram runs for 10 minutes.

The reported amount of spironolactone (expressed as a % of the spironolactone labeled content) is determined by HPLC by reference to a suitable calibration curve.

Particle size measurements were performed on spironolactone (prior to composition manufacture) and on the particulate matter present in the compositions described herein by laser diffraction. The reported particle sizes D(v, 0.1), D(v, 0.5), and D(v, 0.9) relate to the mass median diameter (in µm) of the volume of distribution of the given particles. For instance, D(v, 0.1) (in µm) indicates that 10% of the sample mass is smaller than that value and 90% larger than that value. D(v, 0.5) (in µm) indicates that 50% of the sample mass is smaller than that value and 50% of the sample mass is larger than that value. Finally, D(v, 0.9) (in µm) indicates that 90% of the sample mass is smaller than that value and 10% of the sample mass is larger than that value. Alternatively, particle size can be estimated using optical microscopy.

Viscosity measurements were made in a manner consistent with USP <912> with the following instrument parameters: Helipath T-Bar (S91) with dimensions of 1 mm thick and 48 mm across, spindle speed (60 rpm or 573 rad/sec), 600 mL test substance container having an inner diameter of 85 mm. Results are obtained at 25±1° C. and are presented with units of centi-Poise (cP).

pH was measured in a manner consistent with USP <791>. Typically, a sample was prepared by shaking a sample container for at least 15 seconds with inversion of the container so as to aid sample mixing. A sufficient amount of mixed sample was transferred into a suitable vessel so as to measure the pH.

Anti-microbial effectiveness testing was performed by an independent laboratory in a manner consistent with USP <51>.

Microbiological examination was performed by an independent laboratory in a manner consistent with USP <61> and USP <62>.

Unless stated otherwise, the bottles used for the compositions described herein preferably comprise a polyethylene terephthalate (PETE) resin having an amber color. The amber bottles described herein have volumes of 4 oz. (about 118 mL) or 16 oz (about 473 mL) and have an ultraviolet light (290-450 nm) transmission less than about 10%. The bottles containing the compositions described herein include caps so as to maintain an enclosed composition.

Comparative Example 1

Methylcellulose-containing Composition

A composition similar to U.S. Pat. No. 4,837,211 was prepared. A 40 L batch was manufactured and packaged into 16 oz. amber PETE bottles. The compositional makeup is summarized in Table 1.

TABLE 1

Compositional Makeup of Comparative Example 1

| | Quality Standards | |
|---|---|---|
| Ingredients | mg | % w/v |
| Spironolactone | 5.00 | 0.500 |
| Methylcellulose | 12.00 | 1.200 |
| Simethicone Emulsion | 2.0 | 0.20 |
| Sorbic Acid | 0.50 | 0.050 |
| Potassium Sorbate | 2.00 | 0.200 |
| Saccharin Sodium | 1.35 | 0.135 |
| Sweetener | 0.56 | 0.056 |
| Glycerin | 17.64 | 1.720 |
| Fruit Flavor | 2.00 | 0.200 |
| Purified Water | QS to 1 mL | QS |

The amount of simethicone emulsion in Comparative Example 1 is 0.20% w/v, while the amount of simethicone emulsion found in the composition described in U.S. Pat. No. 4,837,211 is 0.067% w/v.

The spironolactone was dispersed in glycerin and sweetener. Separately, a solution containing methylcellulose (Methocel A4C) in water was cooled to 15° C. for 30 minutes to allow complete hydration of the methylcellulose. The product assayed at 99.2%, 101.5%, and 99.9% for beginning, middle, and end of the packaging process. Table 2 summarizes the observed stability data for the composition of Comparative Example 1 under accelerated and long-term storage conditions.

ASSAY results at three months for accelerated and long-term storage conditions are suspected to be low due to insufficient shaking of the product during sample preparation. It was determined that the method sample preparation required shaking the sample (inverted) for 60 seconds. The low ASSAY values were not confirmed by the 3 month DISSOLUTION results or the 3 month time point for the Resuspendability Tests. These aberrant results highlight the importance of resuspendability of the product.

Resuspendability tests were performed on the product during stability. The purpose of this study was to evaluate the required shake time to provide a uniform product after accelerated (40° C./≤25% RH) and long-term (25° C./40% RH) storage conditions. Table 3 summarizes the assayed amounts (% labeled content ("l.c.")) of spironolactone observed during the Resuspendability Tests.

TABLE 3

Resuspendability Test Results for Comparative Example 1 under Accelerated and Long-Term Storage Conditions

| | % l.c. Spironolactone | | | | | |
|---|---|---|---|---|---|---|
| Shake Time | | Accelerated | | | Long-Term | |
| (sec) | Initial | 1-mo | 2-mo | 3-mo | 2-mo | 3-mo |
| 15 | 84.30 | 59.47 | 76.29 | 74.37 | 79.15 | 59.75 |
| 30 | 96.82 | 77.77 | 87.09 | 82.46 | 94.92 | 75.03 |

TABLE 2

Observed Stability Data for Composition of Comparative Example 1.

| | | Accelerated | | | Long-Term |
|---|---|---|---|---|---|
| Attribute | Initial | 1-mo | 2-mo | 3-mo | 3-mo |
| PHYSICAL INSPECTION | Conforms | Conforms | Conforms | Conforms | Conforms |
| pH | 5.043 | 5.12 | 5.12 | 5.14 | 5.14 |
| SPECIFIC GRAVITY | 1.0093 | 1.0096 | 1.0094 | 1.0097 | 1.0096 |
| DISSOLUTION <711> | | | | | |
| 5 min mean | 89 | 95 | 97 | 95 | 95 |
| % RSD | 3.3 | 0.9 | 2.4 | 0.5 | 1.8 |
| 10 min mean | 92 | 99 | 103 | 100 | 99 |
| % RSD | 3.5 | 0.5 | 0.4 | 1.0 | 0.4 |
| 15 min mean | 93 | 100 | 103 | 100 | 100 |
| % RSD | 3.8 | 0.4 | 0.0 | 0.5 | 0.5 |
| 30 min mean | 93 | 100 | 103 | 101 | 100 |
| % RSD | 3.4 | 0.4 | 0.5 | 0.0 | 0.4 |
| 45 min mean | 93 | 101 | 104 | 101 | 100 |
| % RSD | 3.8 | 0.5 | 0.4 | 0.4 | 1.3 |
| 60 min mean | 93 | 100 | 105 | 101 | 99 |
| % RSD | 3.4 | 0.4 | 1.2 | 0.4 | 2.9 |
| PARTICLE SIZE[a] | | | | | |
| D(v, 0.1) μm | 2.38, 2.36 | 2.18, 2.18 | 2.14, 2.49 | 2.15, 2.13 | 2.13, 2.19 |
| D(v, 0.5) μm | 8.86, 8.83 | 7.97, 7.94 | 7.93, 8.90 | 8.03, 7.96 | 7.60, 7.67 |
| D(v, 0.9) μm | 25.9, 26.1 | 27.3, 29.0 | 26.9, 29.6 | 22.3, 22.1 | 2.1, 20.1 |
| ASSAY (% l.c.) | 101.40, 101.21 | 99.34 | 100.51 | 90.7 | 83.4 |
| REL IMPURITIES (%) | | | | | |
| Canrenone | ND | 0.04 | ND | 0.06 | 0.03 |
| Unidentified | ND | ND | ND | ND | ND |
| Total | ND | 0.04 | ND | 0.06 | 0.03 |
| PRESERVATIVE (% Sorbate) | 102.14 | 95.33 | 94.39 | 94.27 | 94.52 |
| VISCOSITY <912> (cP) | 76.3 | 45.3 | 55.0 | 45.3 | 46.9 |

[a]Reported particle size is of the solid material in the composition.

TABLE 3-continued

Resuspendability Test Results for Comparative Example 1 under Accelerated and Long-Term Storage Conditions

| Shake Time (sec) | % l.c. Spironolactone | | | | | |
|---|---|---|---|---|---|---|
| | Initial | Accelerated | | | Long-Term | |
| | | 1-mo | 2-mo | 3-mo | 2-mo | 3-mo |
| 60 | 101.45 | 97.91 | 99.33 | 93.41 | 100.91 | 90.21 |
| 120 | 100.76 | 100.09 | 101.41 | 103.25 | 100.86 | 102.11 |

Resuspendability Tests (after long-term storage) show upwards of 60-120 seconds of vigorous shaking required to resuspend the spironolactone. This amount of shaking is not a desirable attribute for suspensions because it can lead to poor patient compliance. Further, inadequate resuspension could lead to potentially unwanted dosing errors. In particular, the low viscosities observed for the Comparative Example 1 composition are believed to result in an increase in sedimentation. Thus, it is clear that a balance between viscosity and sedimentation must be achieved highlighting the importance of a certain viscosity range. In view of the excessive shake time required for this composition, efforts were made to identify a suitable suspending agent.

As a part of this effort, seven different compositions containing varying amounts of suspending agents (methylcellulose, xanthan gum, and magnesium aluminometasilicate) were prepared and evaluated. Table 4 summarizes the compositional makeup of seven different compositions.

days. The suspension appeared to be more viscous than the composition of Comparative Example 1 but acceptable. This is a potentially viable composition.

In Comparative Example 4, a 1-L batch containing amorphous magnesium aluminometasilicate (Neusilin®) was added to the Comparative Example 1 composition. After 24 hours, the sedimentation caked at the bottom and did not resuspend easily. This is not a viable composition.

In Comparative Example 5, methylcellulose used in the Comparative Example 1 composition was replaced with xanthan gum (0.13%) and microcrystalline cellulose (Avicel RC-611 at 2.4%) for a 1-L batch. No sedimentation was noted. After 24 hours the suspension became very viscous and non-pourable. Upon shaking, the suspension exhibited shear-thinning properties and became pourable. This is not an ideal composition in terms of practical use.

In Comparative Example 6, methylcellulose used in Comparative Example 1 was replaced with xanthan gum (0.25%) for a 1-L batch. The suspension was elegant and no sedimentation was noted visually after several days. The product appeared to be easily resuspendable. This is a potentially viable composition.

In Comparative Example 7, methylcellulose used in Comparative Example 1 was replaced with xanthan gum (0.25%) and further included magnesium aluminometasilicate (Neusilin®), glycerin, sucralose, propylene glycol, sorbic acid, potassium sorbate, banana flavor, citric acid, sodium citrate, and water in the stated amounts for a 1-L batch. There was no sedimentation noted but significant foaming

TABLE 4

Compositional Makeup of Comparative Examples 2-8

| Ingredients | Comparative Examples | | | | | | |
|---|---|---|---|---|---|---|---|
| | 2 % w/v | 3 % w/v | 4 % w/v | 5 % w/v | 6 % w/v | 7 % w/v | 8 % w/v |
| Spironolactone | 0.500 | 0.500 | 0.500 | 0.500 | 0.500 | 0.500 | 0.500 |
| Methylcellulose | 1.20 | 1.20 | 1.20 | — | — | — | — |
| Xanthan Gum | 0.25 | 0.13 | — | 0.13 | 0.25 | 0.25 | 0.25 |
| Microcrystalline Cellulose[a] | — | — | — | 2.40 | — | — | — |
| MAS[d] | — | — | 0.500 | — | — | 1.00 | 0.50 |
| Simethicone Emulsion | 0.20 | 0.20 | — | 0.20 | 0.20 | — | 0.20 |
| Sorbic Acid | 0.05 | 0.05 | 0.05 | 0.05 | 0.05 | 0.05 | 0.05 |
| Potassium Sorbate | 0.20 | 0.20 | 0.20 | 0.20 | 0.20 | 0.20 | 0.20 |
| Saccharin Sodium | 0.135 | 0.135 | 0.135 | 0.135 | 0.135 | — | 0.135 |
| Sweetener[b] | 0.25 | 0.50 | 0.50 | 0.50 | 0.50 | — | 0.50 |
| Glycerin | 1.764 | 1.764 | 1.764 | 1.764 | 1.764 | 15.00 | 5.00 |
| Fruit Flavor[c] | 0.300 | 0.300 | 0.300 | 0.300 | 0.300 | 0.30 | — |
| Propylene Glycol | — | — | — | — | — | 5.00 | 5.00 |
| Sucralose | — | — | — | — | — | 0.10 | — |
| Citric Acid Anhydrous | — | — | — | — | — | — | 0.20 |
| Sodium Citrate Dihydrate | — | — | — | — | — | — | 0.05 |
| Purified Water | QS | QS | QS | QS | QS | QS | QS |

[a]Microcrystalline Cellulose (Avicel RC-611)
[b]MAS (amorphous magnesium aluminometasilicate, Neusilin ®).
[c]Sweetener (Magnasweet 110)
[d]Fruit Flavor (Banana Flavor)

In Comparative Example 2, a 1-L batch containing xanthan gum (0.25%) was added to the Comparative Example 1 composition. No sedimentation was noted after three days, but the product was very viscous and therefore is not a viable composition. Entrapped air bubbles were also noted in the suspension after three days which could lead to dosing errors.

In Comparative Example 3, a 1-L batch containing xanthan gum (0.13%) was added to the Comparative Example 1 composition. No sedimentation was noted after several (entrapped air bubbles) was visually present after several days. This is not a viable composition.

In Comparative Example 8, methylcellulose used in Comparative Example 1 was replaced with xanthan gum (0.25%) and further included magnesium aluminometasilicate (Neusilin®), glycerin, simethicone, sweetener, sodium saccharin, propylene glycol, sorbic acid, potassium sorbate, sodium citrate, citric acid, banana flavor, and water for a 1-L batch. There was no sedimentation noted after one day. This is a potentially viable composition.

In view of the observations gleaned from the compositions described in Comparative Examples 2-8, xanthan gum at approximately 0.25% appeared to be a suspending agent that provided an elegant easily resuspendable suspension. An added advantage realized by xanthan gum comes from process considerations. For instance, methylcellulose should be sufficiently hydrated prior to use, which requires heating and cooling an aqueous composition containing methylcellulose. There is no such added requirement for xanthan gum. Further development work focuses on the addition of xanthan gum and removal of methylcellulose.

Example 1

Composition that Replaces Methylcellulose with Xanthan Gum

Based on previously mentioned development work, xanthan gum was selected as a potential suspending agent instead of methylcellulose. Table 5 summarizes the compositional makeup of the Example 1 composition.

TABLE 5

Compositional Makeup of Example 1 Composition

| Ingredients | Quality Standards | | |
|---|---|---|---|
| | mg | % w/v | g/Batch |
| Spironolactone | 5.000 | 0.5000 | 50.00 |
| Xanthan Gum | 2.500 | 0.2500 | 25.00 |
| Simethicone Emulsion | 2.000 | 0.2000 | 20.00 |
| Sorbic Acid | 0.5000 | 0.05000 | 5.000 |
| Potassium Sorbate | 2.000 | 0.2000 | 20.00 |
| Saccharin Sodium | 1.350 | 0.1350 | 13.50 |
| Sweetener | 5.000 | 0.5000 | 50.00 |
| Glycerin | 17.64 | 1.764 | 176.4 |
| Fruit Flavor | 3.000 | 0.3000 | 30.00 |
| Purified Water, USP | QS to 1 mL | QS | QS to 10 L |

A 10 L batch was manufactured as follows. Xanthan gum and 7.0 kg of purified water were mixed at 1000 rpm in a first container for 15 minutes. Simethicone emulsion was added to the first container containing xanthan gum, and after addition, the composition was mixed at 1000 rpm for 5 minutes. Next, sorbic acid, potassium sorbate, and sodium saccharin were added to said first container followed by mixing at 900 rpm for 10 minutes. In a separate container, sweetener, glycerin, and 125 g of purified water were mixed at 900 rpm for 1 minute. To said second container, spironolactone was dispersed by mixing at 550 rpm for 5 minutes. The contents of the second container were then transferred to the first container, which was followed by the addition of fruit flavor. The contents of the first container after fruit flavor addition were mixed at 950 rpm for 2 minutes. Finally, the remaining amount of purified water was added to the first container and said contents were mixed at 950 rpm for 15 minutes. The contents of the first container were then packaged into 4 oz. amber PETE bottles. Again, due to the removal of methylcellulose (Methocel A4C), the process is simplified since heating and cooling is not required for xanthan gum.

Table 6 summarizes the observed stability data for the Example 1 composition under accelerated and long-term storage.

TABLE 6

Observed Stability Data for Example 1 under Accelerated and Long-Term Storage Conditions.

| Attribute | Initial | Accelerated | | | Long-Term |
|---|---|---|---|---|---|
| | | 1-mo | 2-mo | 3-mo | 3-mo |
| PHYSICAL INSPECTION | Conforms | Conforms | Conforms | Conforms | Conforms |
| pH | 5.044 | 5.046 | 5.037 | 5.005 | 5.092 |
| SPECIFIC GRAVITY | 1.008 | 1.008 | 1.007 | 1.008 | 1.008 |
| DISSOLUTION <711> | | | | | |
| 5 min mean | 89 | 90 | 91 | 93 | 92 |
| % RSD | 3.6 | 0.7 | 0.9 | 0.4 | 0.0 |
| 10 min mean | 96 | 97 | 98 | 99 | 98 |
| % RSD | 2.6 | 0.5 | 0.6 | 0.0 | 0.4 |
| 15 min mean | 97 | 98 | 99 | 101 | 100 |
| % RSD | 2.6 | 0.4 | 0.5 | 0.0 | 0.6 |
| 30 min mean | 98 | 100 | 99 | 101 | 100 |
| % RSD | 2.5 | 0.0 | 0.4 | 0.4 | 0.0 |
| 45 min mean | 98 | 99 | 100 | 102 | 100 |
| % RSD | 2.6 | 0.4 | 0.6 | 0.4 | 0.0 |
| 60 min mean | 98 | 99 | 99 | 101 | 100 |
| % RSD | 3.0 | 0.6 | 0.5 | 0.5 | 0.0 |
| PARTICLE SIZE$^a$ | | | | | |
| D(v, 0.1) μm | 2.48, 2.47 | 2.21, 2.14 | 2.72, 2.58 | 2.65, 2.64 | 2.72, 2.73 |
| D(v, 0.5) μm | 9.41, 9.47 | 8.84, 8.48 | 9.43, 9.11 | 9.33, 9.11 | 9.63, 9.64 |
| D(v, 0.9) μm | 20.8, 20.9 | 19.8, 19.2 | 20.6, 20.2 | 20.2, 19.7 | 20.9, 20.9 |
| ASSAY (% l.c.) | 99.0 | 99.5 | 101.4 | 103.0 | 101.2 |

TABLE 6-continued

Observed Stability Data for Example 1 under Accelerated and Long-Term Storage Conditions.

| | | Accelerated | | | Long-Term |
|---|---|---|---|---|---|
| Attribute | Initial | 1-mo | 2-mo | 3-mo | 3-mo |
| REL IMPURITIES (%) | | | | | |
| Canrenone | 0.08 | 0.07 | 0.10 | 0.3 | ≤0.10 |
| β-Spironolactone | 0.10 | 0.09 | 0.09 | NR[b] | NR[b] |
| Unidentified | 0.09 | 0.06 | ND | ND | ND |
| Total | 0.27 | 0.22 | 0.19 | 0.3 | ≤0.10 |
| PRESERVATIVE (% Sorbate) | 96.64 | 92.05 | 90.58 | 90.0 | 91.5 |
| VISCOSITY <912> (cP) | 145.0 | 136.5 | 129.7 | 129.3[c] | 145.6 |

NR (not reported), ND (not determined)
[a]Reported particle size is of the solid material in the composition.
[b]β-spironolactone is a process impurity and not reported after 3 months.
[c]After 6-months long-term storage, the observed viscosity is 102.5 cP.

The observed viscosity during the reported time intervals was found to be at least 129 cP. As described elsewhere, the composition should have a viscosity that ranges from 100 cP to 300 cP. Not to be bound by theory, it is believed that a viscosity less than 100 cP promotes sedimentation, which may be problematic with respect to the resuspendability of the pharmaceutical composition. A viscosity greater than 300 cP results in a solution that is too viscous, which may be problematic with respect to product dispensation, i.e., the solution may become too thick to dispense easily.

Resuspendability tests were performed on the Example 1 composition. The purpose of this study was to evaluate the required shake times to provide a uniform product after accelerated and long-term storage conditions. Table 7 summarizes the results of the resuspendability tests.

TABLE 7

Resuspendability Tests (% l.c. spironolactone) for Example 1 Composition under Accelerated and Long-Term Storage Conditions

| | % l.c. Spironolactone | | | | |
|---|---|---|---|---|---|
| | | Accelerated | | | |
| Shake Time (sec) | Initial | 1-mo | 2-mo | 3-mo | 6-mo |
| 5 | — | — | 100.8 | 100.9 | 97.1 |
| 10 | — | — | 101.2 | 100.9 | 103.6 |
| 15 | 99.0 | 99.2 | — | 101.6 | 103.9 |
| 30 | 99.2 | 99.6 | 102.4 | — | — |
| 60 | 98.7 | 99.0 | — | — | — |

| | Long-Term | | | |
|---|---|---|---|---|
| Shake Time (sec) | Initial | Three Months | Six Months | Nine Months | Twelve Months |
| 5 | — | 100.9 | 100.6 | 100.7 | 91.4 |
| 10 | — | 100.9 | 101.7 | 105.9 | 102.3 |
| 15 | 99.0 | 101.6 | 101.7 | 106.3 | 102.7 |
| 30 | 99.2 | — | — | — | — |
| 60 | 98.7 | — | — | — | — |

The stability of the Example 1 composition with xanthan gum (instead of methylcellulose) is acceptable after 3 months accelerated storage. After long-term storage, the product resuspends after only 5 seconds of shaking compared to 60-120 seconds for the composition of Comparative Example 1 (with methylcellulose). The particle size of the composition does not change on stability.

Example 2

Alternate Composition with Xanthan Gum and Citrate Buffer

An alternative composition was manufactured like Example 1, with the exception that a citrate buffer was added. Table 8 summarizes the compositional makeup of the Example 2 composition.

TABLE 8

Compositional Makeup of Example 2 Composition

| | Quality Standards | |
|---|---|---|
| Ingredients | mg | % w/v |
| Spironolactone Micronized | 5.000 | 0.5000 |
| Xanthan Gum | 2.500 | 0.2500 |
| Simethicone Emulsion | 2.000 | 0.2000 |
| Sorbic Acid | 0.5000 | 0.05000 |
| Potassium Sorbate | 2.000 | 0.2000 |
| Saccharin Sodium | 1.350 | 0.1350 |
| Sweetener | 4.000 | 0.4000 |
| Glycerin, USP | 17.64 | 1.764 |
| Fruit Flavor | 3.000 | 0.3000 |
| Citric Acid Anhydrous | 2.388 | 0.2388 |
| Sodium Citrate Dihydrate | 3.696 | 0.3696 |
| Purified Water, USP | QS to 1 mL | QS |

A 12 L batch was manufactured as follows. Xanthan gum and 8.0 kg of purified water were mixed at 900 rpm in a first container for 30 minutes. Simethicone emulsion was added to the first container containing xanthan gum, and after addition, the composition was mixed at 950 rpm for 5 minutes. Next, sorbic acid, potassium sorbate, and sodium saccharin were added to said first container followed by mixing at 950 rpm for 10 minutes. Citric acid and sodium citrate were then added to the first container and the contents were mixed at 1000 rpm for 10 minutes. In a separate container, sweetener, glycerin, and 125 g of purified water were mixed at 400 rpm for 1 minute. To said second container, spironolactone was dispersed by mixing at 1050 rpm for 5 minutes. The contents of the second container were then transferred to the first container, which was followed by the addition of fruit flavor. The contents of the first container after fruit flavor addition were mixed at 1250 rpm for 2 minutes. The remaining amount of purified water (q.s. to 95% of batch) was added to the first container and said contents were mixed at 750 rpm for 5 minutes. An optional step requires checking and adjusting the pH by adding the appropriate amounts of 10% (w/w) citric acid solution or 10% (w/w) sodium citrate solution. The contents of the first container were then packaged into 4 oz. amber PETE bottles.

Observed stability data for the Example 2 composition under accelerated and long-term storage are reported in Tables 9-10, respectively.

TABLE 9

Observed Stability Data for Example 2 under Accelerated Storage Conditions.

| Attribute | Initial | Accelerated | | | |
|---|---|---|---|---|---|
| | | 1 month | 2 months | 3 months | 6 month |
| PHYSICAL INSPECTION | Conforms | Conforms | Conforms | Conforms | Conforms |
| pH | 5.032 | 5.037 | 5.059 | 5.022 | 5.005 |
| SPECIFIC GRAVITY | 1.012 | 1.013 | 1.010 | 1.013 | 1.013 |
| DISSOLUTION <711> | | | | | |
| 5 min mean | 91 | 93 | 91 | 93 | 95 |
| % RSD | 1.3 | 0.9 | 0.8 | 0.4 | 0.0 |
| 10 min mean | 98 | 99 | 97 | 99 | 101 |
| % RSD | 0.5 | 0.5 | 0.4 | 0.4 | 0.0 |
| 15 min mean | 99 | 100 | 98 | 100 | 103 |
| % RSD | 0.4 | 0.5 | 0.4 | 0.8 | 0.5 |
| 30 min mean | 100 | 100 | 98 | 101 | 103 |
| % RSD | 0.5 | 0.4 | 0.5 | 0.0 | 0.0 |
| 45 min mean | 99 | 101 | 99 | 101 | 103 |
| % RSD | 0.5 | 0.5 | 0.0 | 0.4 | 0.5 |
| 60 min mean | 99 | 100 | 99 | 101 | 103 |
| % RSD | 0.4 | 0.5 | 0.0 | 0.0 | 0.0 |
| PARTICLE SIZE[a] | | | | | |
| D(v, 0.1) μm | 2.24, 2.20 | 2.02, 2.03 | 2.39, 2.31 | 2.38, 2.41 | 2.34, 2.07 |
| D(v, 0.5) μm | 8.50, 8.54 | 8.09, 8.18 | 8.55, 8.46 | 8.53, 8.54 | 8.56, 8.32 |
| D(v, 0.9) μm | 18.9, 19.0 | 18.2, 18.3 | 18.7, 18.7 | 18.7, 18.6 | 18.7, 18.5 |
| ASSAY (% l.c.) | 99.4 | 100.4 | 101.0 | 101.4 | 103.8 |
| REL IMPURITIES (%) | | | | | |
| Canrenone | 0.07 | 0.09 | 0.12 | 0.4 | 0.6 |
| β-spironolactone | 0.10 | 0.09 | 0.09 | NR[a] | NR[b] |
| Unidentified | ND | 0.02 | 0.21 | 0.4 | ND |
| Total | 0.17 | 0.20 | 0.21 | 0.40 | 0.6 |
| PRESERVATIVE (% Sorbate) | 98.40 | 95.20 | 98.98 | 92.5 | 89.2 |
| VISCOSITY <912> (cP) | 153.7 | 155.0 | 153.1 | 153.1 | 139.0 |

NR (not reported), ND (not determined)
[a]Reported particle size is of the solid material in the composition.
[b]β-spironolactone is a process impurity and not reported after 3 months.

TABLE 10

Observed Stability Data for Example 2 under Long-Term Storage Conditions.

| Attribute | Initial | Long-Term | | | |
|---|---|---|---|---|---|
| | | 3 months | 6 months | 9 months | 12 months |
| PHYSICAL INSPECTION | Conforms | Conforms | Conforms | Conforms | Conforms |
| pH | 5.032 | 5.052 | 4.988 | 4.961 | 5.000 |
| SPECIFIC GRAVITY | 1.012 | 1.013 | 1.013 | 1.011 | 1.013 |
| DISSOLUTION <711> | | | | | |
| 5 min mean | 91 | 93 | 94 | 93 | 93 |
| % RSD | 1.3 | 0.4 | 0.4 | 0.4 | 0.6 |
| 10 min mean | 98 | 99 | 100 | 99 | 100 |
| % RSD | 0.5 | 0.4 | 0.0 | 0.4 | 1.4 |
| 15 min mean | 99 | 100 | 101 | 100 | 101 |
| % RSD | 0.4 | 0.4 | 0.0 | 0.4 | 0.0 |
| 30 min mean | 100 | 101 | 101 | 101 | 102 |
| % RSD | 0.5 | 0.4 | 0.0 | 0.0 | 0.5 |

TABLE 10-continued

Observed Stability Data for Example 2 under Long-Term Storage Conditions.

| | | Long-Term | | | |
|---|---|---|---|---|---|
| Attribute | Initial | 3 months | 6 months | 9 months | 12 months |
| 45 min mean | 99 | 101 | 101 | 101 | 102 |
| % RSD | 0.5 | 0.4 | 0.0 | 0.4 | 0.0 |
| 60 min mean | 99 | 101 | 101 | 101 | 102 |
| % RSD | 0.4 | 0.4 | 0.4 | 0.0 | 0.5 |
| PARTICLE SIZE[a] | | | | | |
| D(v, 0.1) μm | 2.24, 2.20 | 2.31, 2.36 | 2.39, 2.36 | 2.17, 2.24 | 2.17, 2.20 |
| D(v, 0.5) μm | 8.50, 8.54 | 8.49, 8.54 | 8.61, 8.57 | 7.96, 8.08 | 8.05, 8.14 |
| D(v, 0.9) μm | 18.9, 19.0 | 18.7, 18.7 | 18.8, 18.7 | 17.5, 17.5 | 17.6, 16.8 |
| ASSAY (% l.c.) | 99.4 | 101.6 | 102.3 | 103.3 | 102.9 |
| REL IMPURITIES (%) | | | | | |
| Canrenone | 0.07 | 0.09 | 0.12 | 0.4 | 0.1 |
| β-spironolactone | 0.10 | 0.09 | 0.09 | NR[b] | NR[b] |
| Unidentified | ND | 0.02 | 0.21 | 0.4 | 0.1 |
| Total | 0.17 | 0.20 | 0.21 | 0.40 | 0.1 |
| PRESERVATIVE (% Sorbate) | 98.40 | 95.20 | 98.98 | 92.5 | 96.7 |
| VISCOSITY <912> (cP) | 153.7 | 162.5 | 152.2 | 161.5 | 164.1 |

NR (not reported), ND (not determined)
[a]Reported particle size is of the solid material in the composition.
[b]β-spironolactone is a process impurity and not reported after 3 months.

The observed viscosity during the reported time intervals was found to be at least 139 cP. As stated above, the composition should have a viscosity that ranges from 100 cP to 300 cP.

As stated above, Pramar et al., *Journal of Clinical Pharmacy and Therapeutics* (1992): 17(4): 245-248 report stabilities studies of a spironolactone-containing liquid dosage form containing phosphate (0.05, pH=4.5±0.1) and citrate buffer (0.05 M, pH=4.5±0.1). After 93-days of storage at 40° C., Pramar et al. found that the amount of spironolactone remaining in the phosphate-buffered dosage form to be 91.23±0.51%, while the citrate-buffered dosage form to be 80.97±0.84%. In view of the findings reported by Pramar et al., it was surprising that the addition of citrate buffer resulted in a composition that had an acceptable impurity profile after accelerated and long-term storage.

Resuspendability tests were performed on the Example 2 composition. The purpose of this study was to evaluate the required shake times to provide a uniform product after accelerated and long-term storage conditions. Table 11 summarizes the results of the resuspendability tests.

TABLE 11

Resuspendability Tests (% l.c. spironolactone) for Example 2 Composition under Accelerated and Long-Term Storage Conditions

| | % l.c. Spironolactone | | | | |
|---|---|---|---|---|---|
| | | Accelerated | | | |
| Shake Time (sec) | Initial | 1-mo | 2-mo | 3-mo | 6-mo |
| 5 | — | — | 102.6 | 99.0 | 98.8 |
| 10 | — | — | 102.6 | 101.1 | 103.0 |
| 15 | 98.5 | 98.9 | 100.9 | 98.9 | 102.7 |
| 30 | 98.4 | 98.9 | — | — | — |
| 60 | 98.4 | 98.6 | — | — | — |

TABLE 11-continued

Resuspendability Tests (% l.c. spironolactone) for Example 2 Composition under Accelerated and Long-Term Storage Conditions

| | | Long-Term | | | |
|---|---|---|---|---|---|
| Shake Time (sec) | Initial | 3-mo | 6-mo | 9-mo | 12-mo |
| 5 | — | 104.4 | 101.8 | 100.9 | 97.3 |
| 10 | — | 101.5 | 101.6 | 101.3 | 102.2 |
| 15 | 98.5 | 103.5 | 101.6 | 101.1 | 102.8 |
| 30 | 98.4 | — | — | — | — |
| 60 | 98.4 | — | — | — | — |

The results presented in Table 11 show that the Example 2 composition resuspends within 5 seconds after shaking under accelerated and long-term storage.

Figure 2:
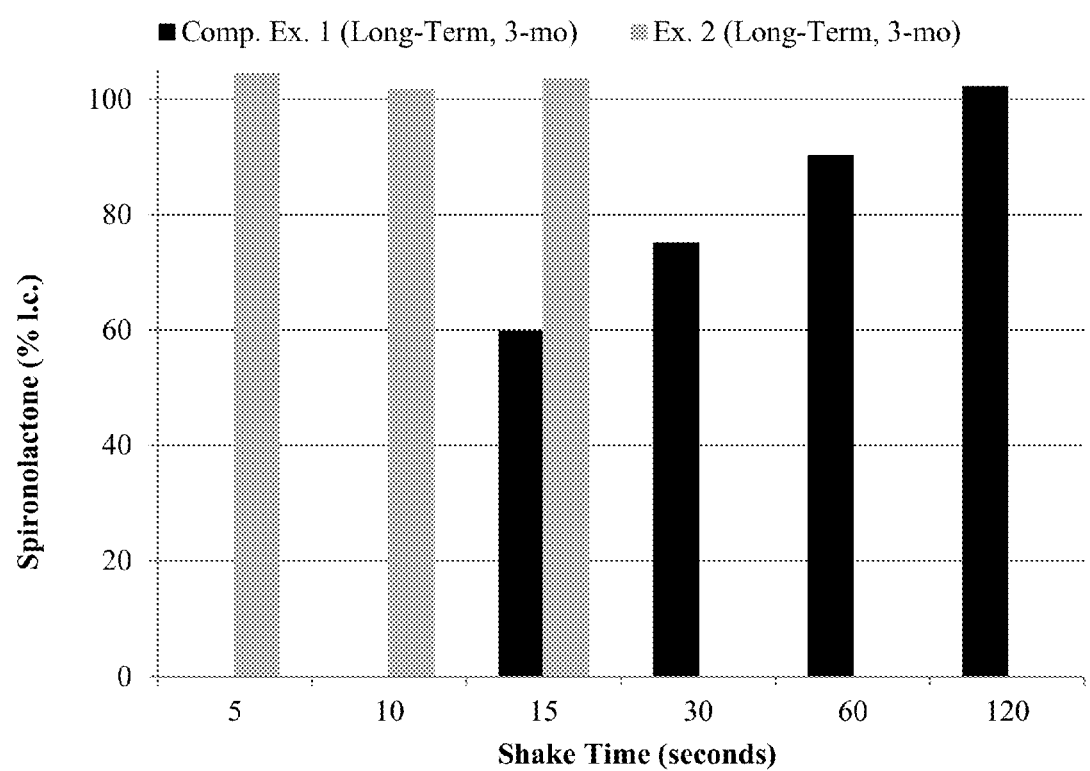
FIG. 2 shows the observed spironolactone content (% l.c.) as a function of shake-time (in seconds) for the compositions of Example 2 (grey bar) and Comparative Example 1 (black bars) after storage at 25±2° C. and 40±5% relative humidity for 3-months.

As a point of reference, FIG. 1 shows the initially observed spironolactone content (% l.c.) as a function of shake-time (in seconds) for the compositions of Example 2 (grey bars) and Comparative Example 1 (black bars). FIG. 2 shows the observed spironolactone content (% l.c.) as a function of shake-time (in seconds) for the compositions of Example 2 (grey bars) and Comparative Example 1 (black bars) after long-term storage for 3-months. The data depicted in FIG. 2 shows that the composition of Example 2 remains suspended with uniform content even after long-term storage for 3-months. This should be contrasted to the composition of Comparative Example 1 in which uniform suspension requires a shake-time of at least 120 seconds.

The composition of Example 2 was assayed for spironolactone after shaking well and after allowing the bottle to remain undisturbed for 30 minutes, 2 hours, and 4 hours to evaluate the uniformity of the spironolactone under actual conditions of use. The spironolactone remains suspended and uniform for at least 4 hours after initial shaking. No sedimentation is visually observed even after seven days. Table 12 summarizes the suspension maintenance test for the Example 2 composition after initial shaking.

TABLE 12

Suspension Maintenance Tests for Example
2 Composition after Initial Shaking

| Time point | % l.c. Spironolactone |
|---|---|
| Initial | 101.2 |
| 30 minutes | 101.1 |
| 2 hours | 101.1 |
| 4 hours | 101.0 |

The stability of the Example 2 composition with xanthan gum and citrate buffer is acceptable after 3 months accelerated conditions. After long term storage the product resuspends after only 5 seconds of shaking compared to 60-120 seconds in the composition described in Comparative Example 1. The product remains suspended and uniform for at least four hours after shaking well. Improvements in the resuspendability of the product are achieved with this composition.

Figure 3:
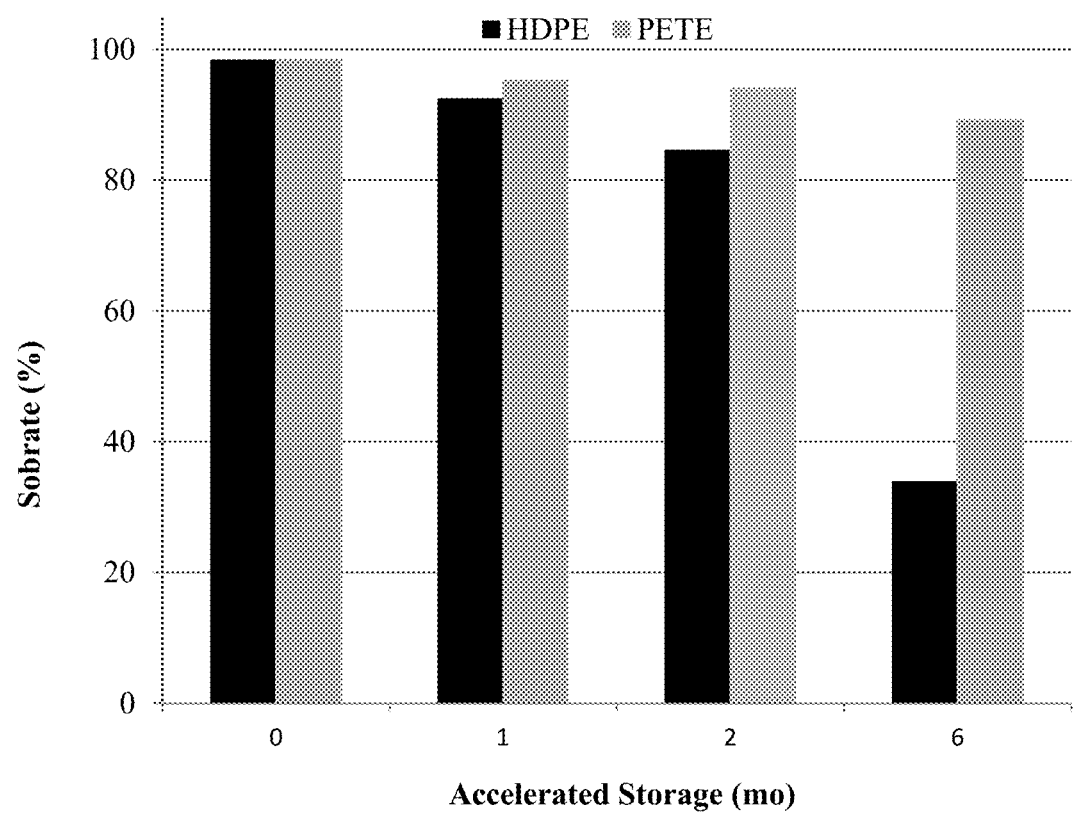
FIG. 3 shows the effect of storage at 40±2° C. and not more than 25% relative humidity on sorbate levels in amber PETE bottles (grey bars, Example 2 Composition) and white HDPE bottles (black bars, composition similar to Comparative Example 1).

Use of amber PETE bottles, instead of white HDPE bottles, reduced the rate of loss for sorbate. A composition similar to Comparative Example 1 (except that glycerin and fruit flavor were present at 1.717 and 0.10% w/v, respectively), was stored in two separate bottles: amber PETE and white HDPE. The amount of sorbate (%) in the composition stored in the PETE bottle after long-term storage at 9-months was about 90.7%. The amount of sorbate (%) in the composition stored in the HDPE bottle after long-term storage at 6-months was about 56.7%. In view of these results, a decision was made to use amber PETE bottles due to the extensive sorbate loss in the HDPE bottles. As a point of reference, FIG. 3 shows the effect of storage on sorbate levels in amber PETE bottles (grey bars, Example 2 Composition) and white HDPE bottles (black bars, above-mentioned composition similar to Comparative Example 1). Acceptable sorbate levels are observed in the amber PETE bottles after six months accelerated storage. This should be contrasted to the composition contained in the white HDPE bottles.

The importance of preservative level is apparent from a preservative effectiveness study. In that study, compositions identical to the Example 2 composition were prepared (except for varying levels of total sorbate (approximately 25%, 50%, and 75%), where total sorbate is the amount of sorbic acid and potassium sorbate). Antimicrobial Effectiveness Testing showed that at a total sorbate level of about 25%, the composition passed against *E. coli, P. aeruginosa, S. aureus*, and *A. brasiliensis*, but failed against *B. cepacia* and *C. albicans*. Antimicrobial Effectiveness Testing showed that at total sorbate levels of 50%, the composition passed against *E. coli, P. aeruginosa, S. aureus*, and *A. brasiliensis*, and *C. albicans*, but failed against *B. cepacia*. Finally, Antimicrobial Effectiveness Testing showed that at total sorbate levels of 75%, the composition passed against *E. coli, P. aeruginosa, S. aureus*, and *A. brasiliensis, C. albicans*, and *B. cepacia*. And, 100% sorbate levels the composition passed against all of the above-mentioned organisms.

The stability of the Example 2 composition with xanthan gum (instead of methylcellulose) is acceptable after 6 months accelerated storage conditions and 12 months long term storage conditions. After long term storage, the product resuspends to a suitable level after only 5 seconds of shaking compared to 60-120 seconds observed for the composition of Comparative Example 1 (with methylcellulose). After nine months of long-term storage visual sedimentation is seen at the bottom of the bottle for the composition of Example 1 that is not noted in the buffered system (Example 2). This observation is confirmed by long-term storage resuspendability tests at 9-months (with no shaking) for the Example 1 composition (16.4% l.c.) and the Example 2 composition (89.1% l.c.) This is a surprising discovery that after long-term storage the Example 2 composition exhibits a much higher level of uniformity without shaking, which suggests that the citrate buffer is serving to retard the sedimentation rate. Improvements in the resuspendability of the product is seen even in the 4 oz. PETE bottle. The particle size of the Example 2 composition does not change on stability. Improvements and simplification in the process are also gained by replacing the methylcellulose with xanthan gum.

Another point of interest stems from the observed viscosity values for the Example 1 and Example 2 compositions under accelerated storage conditions. For instance, the Example 1 composition (without citrate buffer) after 6-months at accelerated storage had an observed viscosity of 102.5 cP. This should be contrasted to the Example 2 composition (with citrate buffer) after 6-months at accelerated storage where the observed viscosity was 139.0 cP. This amounts to a change in viscosity of about 36%. This was an unexpectedly surprising finding, which provided the motivation to pursue further a composition that contains a citrate buffer.

It is also of interest to compare the viscosity values for the compositions of Comparative Example 1, Example 1, and Example 2, after 3-months of storage under accelerated conditions. For example, the observed viscosity value for the Comparative Example 1 composition was 45.3 cP, after 3-months storage under accelerated conditions. At the same time point and the same conditions, the observed viscosity values for the Example 1 and Example 2 compositions were 129.3 cP and 153.1 cP, respectively. This information shows the unexpected superiority of xanthan gum with respect to methylcellulose.

Examples 3-4

Spironolactone Compositions Containing Different Amounts of Xanthan Gum

Two different compositions with different amounts of xanthan gum were prepared and different viscosities. The compositional makeup of Example 3 and Example 4 is summarized in Table 13.

TABLE 13

Compositional Makeup of Examples 3-4

| | Quality Standards | | | |
|---|---|---|---|---|
| | Example 3 | | Example 4 | |
| Ingredients | mg | % w/v | mg | % w/v |
| Spironolactone Micronized | 5.000 | 0.5000 | 5.000 | 0.5000 |
| Xanthan Gum | 1.800 | 0.1800 | 3.600 | 0.3600 |
| Simethicone Emulsion | 2.000 | 0.2000 | 2.000 | 0.2000 |
| Sorbic Acid | 0.5000 | 0.05000 | 0.5000 | 0.05000 |
| Potassium Sorbate | 2.000 | 0.2000 | 2.000 | 0.2000 |
| Saccharin Sodium | 1.350 | 0.1350 | 1.350 | 0.1350 |
| Sweetener | 4.000 | 0.4000 | 4.000 | 0.4000 |
| Glycerin, USP | 17.64 | 1.764 | 17.64 | 1.764 |
| Fruit Flavor | 3.000 | 0.3000 | 3.000 | 0.3000 |
| Citric Acid Anhydrous | 2.010 | 0.201 | 2.010 | 0.201 |

TABLE 13-continued

Compositional Makeup of Examples 3-4

| | Quality Standards | | | |
|---|---|---|---|---|
| | Example 3 | | Example 4 | |
| Ingredients | mg | % w/v | mg | % w/v |
| Sodium Citrate Dihydrate | 4.280 | 0.4280 | 4.280 | 0.4280 |
| Purified Water, USP | QS to 1 mL | QS | QS to 1 mL | QS |
| Viscosity (cP) | | 108.0 | | 299.4 |
| pH | | 4.8 | | 4.9 |

The compositions of Examples 3-4 were assayed for spironolactone after shaking well and after allowing the bottle to remain undisturbed for 30 minutes, 2 hours, and 4 hours to evaluate the uniformity of the spironolactone under actual conditions of use. The spironolactone remains suspended and uniform for at least 4 hours after initial shaking. No sedimentation is visually observed even after seven days. The results are found in Table 14.

TABLE 14

Suspension Maintenance Tests for Example 3-4 Compositions after Initial Shaking

| | % l.c. Spironolactone | |
|---|---|---|
| Time point | Example 3 | Example 4 |
| Initial | 102.4 | 101.5 |
| 30 minutes | 102.1 | 101.2 |
| 2 hours | 101.2 | 101.1 |
| 4 hours | 102.1 | 101.0 |

In view of these results, a viscosity range of 100 to 300 cP was found to be acceptable.

Example 5

Composition Containing Xanthan Gum and Citrate Buffer

An alternative composition was manufactured like Example 2 except at a larger (250 L) scale. Table 15 summarizes the compositional makeup of the Example 5 composition.

TABLE 15

Compositional Makeup of Example 5

| Ingredients | mg | % w/v |
|---|---|---|
| Spironolactone | 5.000 | 0.5000 |
| Xanthan Gum | 2.500 | 0.2500 |
| Simethicone Emulsion | 2.000 | 0.2000 |
| Sorbic Acid | 0.5000 | 0.05000 |
| Potassium Sorbate | 2.000 | 0.2000 |
| Saccharin Sodium | 1.350 | 0.1350 |
| Sweetener[a] | 4.000 | 0.4000 |
| Glycerin | 17.64 | 1.764 |
| Fruit Flavor[b] | 3.000 | 0.3000 |
| Citric Acid Anhydrous | 1.758 | 0.1758 |

TABLE 15-continued

Compositional Makeup of Example 5

| Ingredients | mg | % w/v |
|---|---|---|
| Sodium Citrate Dihydrate | 4.660 | 0.4660 |
| Purified Water | QS to 1 mL | QS |
| pH | 4.5-5.5[c,d] | |

[a]Sweetener (Magnasweet 110)
[b]Fruit Flavor (Banana Flavor).
[c]pH adjustment with 10% (w/w) Citric Acid Solution or 10% (w/w) Sodium Citrate Solution, if necessary.
[d]The in process pH specification for manufacture was pH of 4.8 to 5.2, but with storage the pH specification is 4.5 to 5.5.

Three separate batches (250 L each) were prepared in a manner comparable to that described for the Example 2 composition. The average viscosity of the three batches was determined to be 155±2 cP, while the average specific gravity was determined to be 1.012±0.001. The measured bulk pH was 5.0 for each batch.

Each batch was packaged in amber PETE containers (4 oz. (118 mL fill volume) and 16 oz. (473 mL fill volume)). The stability of the Example 5 Composition with xanthan gum is acceptable after accelerated (6-months) and long-term (12-months) storage. Particle size and viscosity values were consistent to those values reported for the Example 2 composition for accelerated and long-term storage. Resuspendability tests show that the Example 5 composition resuspends within 5-15 seconds after accelerated and long-term storage. The results for a portion of the packaged batch (4 oz.) is summarized in Table 16.

TABLE 16

Resuspendability Tests (% l.c. spironolactone) for Example 5 Composition under Accelerated and Long-Term Storage Conditions

| | % l.c. Spironolactone | | | | |
|---|---|---|---|---|---|
| | | Accelerated | | | |
| Shake Time (sec) | Initial | 1-mo | 2-mo | 3-mo | 6-mo |
| 5 | 100.5 | 101.1 | 102.0 | 102.9 | 101.9 |
| 10 | 100.4 | 101.7 | 101.7 | 103.3 | 103.0 |
| 15 | 100.5 | 101.5 | 102.3 | 103.4 | 103.9 |

| | | Long-Term | | | |
|---|---|---|---|---|---|
| Shake Time (sec) | Initial | 3-mo | 6-mo | 9-mo | 12-mo |
| 5 | 100.5 | 101.2 | 100.8 | 99.5 | 104.0 |
| 10 | 100.4 | 102.3 | 102.6 | 102.5 | 104.1 |
| 15 | 100.5 | 102.2 | 101.0 | 102.6 | 103.6 |

The data found in Table 16 shows that the Example 5 composition exhibits satisfactory resuspendability even after 12-months of long-term storage. The slight, but acceptable, increase in % l.c. spironolactone is believed to be due to evaporative loss. For instance, after 3-months long-term storage a weight loss of about 0.4% was observed, while after 12-months long-term storage a weight loss of about 1.6% was observed. A weight loss of not more than 5% at accelerated conditions is considered to be acceptable.

Example 6

Composition with Xanthan Gum and Citrate Buffer

A composition is manufactured like Example 5 except at a larger (2000 L) scale. Table 17 summarizes the compositional makeup of the Example 6 composition.

TABLE 17

Compositional Makeup of Example 6

| Ingredients | mg | % w/v | % w/w[a] |
|---|---|---|---|
| Spironolactone | 5.000 | 0.5000 | 0.4941 |
| Xanthan Gum | 2.500 | 0.2500 | 0.2470 |
| Simethicone Emulsion | 2.000 | 0.2000 | 0.1976 |
| Sorbic Acid | 0.500 | 0.05000 | 0.04941 |
| Potassium Sorbate | 2.000 | 0.2000 | 0.1976 |
| Saccharin Sodium | 1.350 | 0.1350 | 0.1334 |
| Sweetener[b] | 4.000 | 0.4000 | 0.3953 |
| Glycerin | 17.64 | 1.764 | 1.743 |
| Fruit Flavor[c] | 3.000 | 0.3000 | 0.2964 |
| Citric Acid Anhydrous | 2.010 | 0.2010 | 0.1986 |
| Sodium Citrate Dihydrate | 4.280 | 0.4280 | 0.4229 |
| Purified Water | QS to 1 mL | QS | QS |
| pH | | 4.5-5.5[d,e] | |

[a]Calculated using a specific gravity of 1.012.
[b]Sweetener (Magnasweet 110).
[c]Fruit Flavor (Banana Flavor).
[d]pH adjustment with 10% (w/w) Citric Acid Solution or 10% (w/w) Sodium Citrate Solution, if necessary
[e]The in process pH specification for manufacture was pH of 4.8 to 5.0, but with storage the pH specification is 4.5 to 5.5.

Alternative embodiments, examples, and modifications which would still be encompassed by the disclosure may be made by those skilled in the art, particularly in light of the foregoing teachings. Further, it should be understood that the terminology used to describe the disclosure is intended to be in the nature of words of description rather than of limitation.

The subject matter of U.S. Provisional Patent Application No. 62/495,583, filed on Oct. 30, 2015, is incorporated by reference in its entirety. Additionally, the references described herein are incorporated by reference in their entirety to the extent necessary. In the event that there is a difference in meaning between the incorporated terms and the terms disclosed herein, the meaning of the terms disclosed herein will control.

Those skilled in the art will also appreciate that various adaptations and modifications of the preferred and alternative embodiments described above can be configured without departing from the scope and spirit of the disclosure. Therefore, it is to be understood that, within the scope of the appended claims, the disclosure may be practiced other than as specifically described herein.

We claim:

1. A pharmaceutical composition, comprising:
 (a) 0.50% w/v of spironolactone;
 (b) from 0.18% w/v to 0.36% w/v of a xanthan gum;
 (c) an anti-foaming agent comprised of 0.20% w/v of a simethicone emulsion;
 (d) a preservative comprised of from 0.025% w/v to 0.050% w/v of sorbic acid and from 0.10% w/v to 0.20% w/v of potassium sorbate;
 (e) a dispersing agent comprised of from 2.0% w/v to 2.2% w/v glycerin;
 (f) a sweetening agent comprises 0.14% w/v sodium saccharin and from 0.03% w/v to 0.04% w/v ammonium glycyrrhizinate;
 (g) a flavoring agent in an amount that ranges from 0.1% w/v to 0.5% w/v;
 (h) a buffer to maintain the pH of the pharmaceutical composition from 4.5 to 5.5;
 wherein the buffer is comprised of from 0.17% w/v to 0.24% w/v citric acid and from 0.36% w/v to 0.48% w/v of a citrate salt; and
 (i) a sufficient amount of a water vehicle.

2. The pharmaceutical composition of claim 1, wherein the viscosity of the composition ranges from 100 cP to 300 cP.

3. The pharmaceutical composition of claim 1, wherein the anti-foaming agent (c) is comprised of 0.20% w/v of a simethicone emulsion;
 the preservative (d) is comprised of 0.050% w/v of sorbic acid and 0.20% w/v of potassium sorbate;
 the dispersing agent (e) is comprised of 2.1% w/v to 2.2% w/v glycerin; and
 wherein the pharmaceutical composition comprises the buffer comprised of 0.20% w/v citric acid and 0.43% w/v sodium citrate.

4. The pharmaceutical composition of claim 3, wherein xanthan gum is present in an amount of 0.25% w/v.

5. The pharmaceutical composition of claim 4, wherein the viscosity of the composition ranges from 130 cP to 170 cP.

6. The pharmaceutical composition of claim 4, wherein the pH of the pharmaceutical composition ranges from 4.8 to 5.2.

7. An enclosed, amber polyethylene terephthalate (PETE) bottle comprising the composition of claim 4.

8. The PETE bottle of claim 7, wherein the volume of said bottle is 4 oz. or 16 oz.

9. A process for preparing the pharmaceutical composition of claim 1, which comprises:
 (1) mixing the xanthan gum, anti-foaming agent, preservative, a portion of the sweetening agent, and, the buffer, in water in a first container;
 (2) mixing the spironolactone, the dispersing agent, and the remaining portion of the sweetening agent in a second container;
 (3) transferring the contents of the second container to the first container followed by mixing the contents of the first container;
 (4) adding the flavoring agent to the contents of the first container from step (3);
 (5) adding water to the first container of step (3) and mixing the contents of the first container;
 and
 (6) dispensing the contents of the first container from step (5) into an amber polyethylene terephthalate bottle.

10. A pharmaceutical product prepared by the process as claimed in claim 9.

11. A method for the treatment of hypertension in a subject in need thereof, which comprises administering to the subject a therapeutically effective amount of the pharmaceutical composition of claim 1.

12. The method of claim 11, wherein the composition is administered orally or by a nasogastric tube.

13. A method for the treatment of severe heart failure in a subject in need thereof, which comprises administering to the subject a therapeutically effective amount of the pharmaceutical composition of claim 1;
 wherein the composition is administered orally or by a nasogastric tube.

14. A pharmaceutical composition comprising: (a) 0.50% w/v spironolactone; (b) 0.25% w/v of a xanthan gum; (c) 0.20% w/v of a simethicone emulsion; (d) a preservative comprised of 0.050% w/v of sorbic acid and 0.20% w/v of potassium sorbate; (e) from 2.1% w/v to 2.2% w/v glycerin; (f) a sweetening agent containing 0.14% w/v sodium saccharin and from 0.03% w/v to 0.04% w/v ammonium glycyrrhizinate; (g) 0.30% w/v of a fruit flavoring agent; (h) a buffer comprised of 0.20% w/v citric acid and 0.43% w/v sodium citrate; and (i) a sufficient amount of a water vehicle.

15. The pharmaceutical composition of claim 14, said composition having a pH of from 4.5 to 5.5.

16. The pharmaceutical composition of claim 14, said composition having a pH of from 4.8 to 5.2.

17. The pharmaceutical composition of claim 14, said composition having a viscosity that ranges from 100 cP to 300 cP.

18. The pharmaceutical composition of claim 14, said composition having a viscosity that ranges from 130 cP to 170 cP.

19. An enclosed, amber polyethylene terephthalate (PETE) bottle having a volume of 4 oz or 16 oz comprising the composition of claim 14.

20. A method for the treatment of hypertension in a subject in need thereof, which comprises administering to the subject a therapeutically effective amount of the pharmaceutical composition of claim 14.

21. The method of claim 14, wherein the composition is administered orally or by a nasogastric tube.

22. A method for the treatment of severe heart failure in a subject in need thereof, which comprises administering to the subject a therapeutically effective amount of the pharmaceutical composition of claim 14;
wherein the composition is administered orally or by a nasogastric tube.

23. A method for the treatment of a patient suffering from a skin disorder, which comprises administering to the subject a therapeutically effective amount of the pharmaceutical composition of claim 14, wherein said skin disorder is selected from the group consisting of acne, hirsutism, androgenic alopecia, rosacea, and combinations thereof.

24. The pharmaceutical composition of claim 1, wherein the spironolactone content is 100±10% of labeled content when stored under 40° C. and not more than 25% relative humidity for 6-months.

25. The pharmaceutical composition of claim 14, wherein the spironolactone content is 100±10% labeled content when stored under 40° C. and not more than 25% relative humidity for 6-months.

26. The pharmaceutical composition of claim 1, wherein the spironolactone content is 100±10% of labeled content when stored under 25° C. and 40% relative humidity for 24-months.

27. The pharmaceutical composition of claim 14, wherein the spironolactone content is 100±10% of labeled content when stored under 25° C. and 40% relative humidity for 24-months.

\* \* \* \* \*